US007208141B2

(12) United States Patent
Montgomery

(10) Patent No.: US 7,208,141 B2
(45) Date of Patent: *Apr. 24, 2007

(54) INHALABLE AZTREONAM AEROSOL FOR TREATMENT AND PREVENTION OF PULMONARY BACTERIAL INFECTIONS

(75) Inventor: Alan Bruce Montgomery, Seattle, WA (US)

(73) Assignee: Corus Pharma, Inc., Seattle, WA (US)

( * ) Notice: Subject to any disclaimer, the term of this patent is extended or adjusted under 35 U.S.C. 154(b) by 374 days.

This patent is subject to a terminal disclaimer.

(21) Appl. No.: 10/654,815

(22) Filed: Sep. 4, 2003

(65) Prior Publication Data

US 2005/0129623 A1    Jun. 16, 2005

Related U.S. Application Data

(62) Division of application No. 10/027,113, filed on Dec. 20, 2001, now Pat. No. 6,660,249.

(60) Provisional application No. 60/258,423, filed on Dec. 27, 2000.

(51) Int. Cl.
*A61K 9/00* (2006.01)
*A61K 9/12* (2006.01)
*A61K 9/14* (2006.01)

(52) U.S. Cl. .......................... 424/45; 424/46; 424/489; 514/2; 128/203.15

(58) Field of Classification Search ................ 424/45, 424/46, 489; 514/2; 128/203.15
See application file for complete search history.

(56) References Cited

U.S. PATENT DOCUMENTS

| | | | |
|---|---|---|---|
| 4,550,105 A | 10/1985 | Matsuo et al. | 514/210 |
| 4,572,801 A | 2/1986 | Matsuo, deceased et al. | 260/245.4 |
| 4,610,824 A | 9/1986 | Truner | 540/335 |
| 4,673,739 A | 6/1987 | Matsuo, deceased et al. | 540/355 |
| 4,775,670 A | 10/1988 | Sykes et al. | 514/210 |
| 4,946,838 A | 8/1990 | Floyd et al. | 514/210 |
| 5,662,929 A * | 9/1997 | Lagace et al. | 424/450 |
| 5,875,776 A | 3/1999 | Vaghefi | 128/203.15 |
| 6,518,239 B1 | 2/2003 | Kuo et al. | 514/2 |
| 2004/0009126 A1 | 1/2004 | Pilkiewicz et al. | 424/46 |
| 2004/0062721 A1* | 4/2004 | Montgomery | 424/46 |

FOREIGN PATENT DOCUMENTS

| | | | |
|---|---|---|---|
| EP | 02975801 | 1/1999 | |
| WO | WO 0134232 | 5/2001 | 11/0 |

OTHER PUBLICATIONS

Despina Daisy Frangolias, et al., *Burkholderia cepacia* in Cystic Fibrosis, *Am. J or Respir Crit Care Med.* 160:1572-1577 (1999).

Diane H. Johnson, et al., Aztreonam, *Medical Clinics of North America*, 79/4:733-743 (Jul. 4, 1995).
Woo, M.S., et al., Use of Aersolized Aztreonam in CF Lung Transplant Pateints Colonized With *Burkholderia cepacia*, 2002 Cystic Fibrosis Conference, p. 322:419.
Petra Borsje, MD, et al., Aerosol Therapy in Cystic Fibrosis: A Survey of 54 CF Centers, *Pediatric Pulmonology*, 30:368-376 (2000).
Rafael Canton, PD, PhD, et al., Lung Colonization With *Enterobacteriaceae* Producing Extended-Spectrum β-Lactamases in Cystic Fibrosis Patients, *Pediatric Pulmonology*, 24:213-217 (1997).
S. Ballestero, et al., *Stenocrophomonas maltiphilia* in Cystic Fibrosis Patients, p. 12, 20th European Cystic Fibrosis Conference, Brussels, Belgium, (Jun. 18-21, 1995).
Sira Carrasco, et al., The General Approach to Cystic Fibrosis Pulmonary Infection in Spain, *Cystic Fibrosis Pulmonary Infections: Lessons From Around the World*, Chapter 18, pp. 223-230 (1996).
Brian E. Scully, M.B., et al., Use of Aztreonam in the Treatment of Serious Infections Due to Multiresistant Gram-Negative Organisms, Including *Pseudomonas Aeruginosa*, *The American Journal of Medicine*, 78:251-261 (Feb. 1985).
John A. Bosso, et al., Efficacy of Aztreonam in Pulmonary Exacerbations of Cystic Fibrosis, *The Pediatr. Infect. Dis. J.*, 6:393-397 (1987).
James L. Cook, M.D., Gram-Negative Bacillary Pneumonia in the Nosocomial Setting, *The American Journal of Medicine*, 88:3C-34S-37S.
A. Boccazzi, et al., The Pharmacokinetics of Aztreonam and Penetration into the Bronchial Secretions of Critically Ill Patients, *Journal of Antimicrobial Chemotherapy*, 23:401-407, (1989).
Harold C. Neu, M.D., Aztreonam Activity, Pharmacology and Clinical Uses, *The American Journal of Medicine*, 88:3C-2S-3C-6S.
John J. LiPuma, MD, *Burkholderia cepacia*, Management Issues and New Insights, *Clinics in Chest Medicine*, 19/3:473-486 (Sep. 1998).
Stephen C. Aronoff, et al., *In Vitro* Activities of aztreonam, Piperacillin, and Ticarcillin Combined with Amikacin Against Amikacin-Resistant *Pseudomonas aeruginosa* and *P. cepacia* Isolates from Children with Cystic Fibrosis, *Antimicrobial Agents and Chemotherapy*, 25/2:279-280 (Feb. 1984).

(Continued)

*Primary Examiner*—Johann Richter
*Assistant Examiner*—Mina Haghighatian
(74) *Attorney, Agent, or Firm*—Hana Verny; Peters Verny, LLP

(57) ABSTRACT

A method and a composition for treatment of pulmonary bacterial infections caused by gram-negative bacteria suitable for treatment of infection caused by *Escherichia coli, Klebsiella pneumoniae, Klebsiella oxytoca, Pseudomonas aeruginosa, Haemophilus influenzae, Proteus mirabilis, Enterobacter* species, *Serratia marcescens* as well as those caused by *Burkholderia cepacia, Stenotrophomonas maltophilia, Alcaligenes xylosoxidans*, and multidrug resistant *Pseudomonas aeruginosa*, using a concentrated formulation of aztreonam, or a pharmaceutically acceptable salt thereof, delivered as an aerosol or dry powder formulation.

30 Claims, No Drawings

OTHER PUBLICATIONS

John A. Bosso, et al., *In Vitro* Acitivities of Combinations of Aztreonam, Ciprofloxacin, and Ceftazidime Against Clinical Isolates of *Pseudomonas aeruoginosa* and *Pseudomonas cepacia* from Patients with Cystic Fibrosis, *Antimicrobial Agents and Chemotherapy*, 34/3:487-488 (Mar. 1990).

John M. Matsen, et al., The Use of Aztreonam in the Cystic Fibrosis Patient, *Pediatr. Infect. Dis. J.*, 8/9:S117-S119 (1989).

Lisa Saiman, MD, Antimicrobial Resistance Among *Burkholderia stenotrophomonas* and Alcaligenes isolates Studied by the CF Eferal Center for Susceptibility and Synergy Testing, 1998 Cystic Fibrosis Conference, Symposium Session Summaries, 118-119 (1998).

Preston W. Campbell III, MD., et al., Use of Aerosolled Antibiotics in Patients with Cystic Fibrosis, Consensus Conference, pp. 775-789 (Sep. 1999).

Dapena Fernandez J., et al., Inhaled Aztreonam Therapy in Patients with Cystic Fibrosis Colonized with *Pseudomonas aeruginosa*, Spanish Annals on Pediatrics, 40/3 (1993).

* cited by examiner

INHALABLE AZTREONAM AEROSOL FOR TREATMENT AND PREVENTION OF PULMONARY BACTERIAL INFECTIONS

This application is a Divisional of the U.S. application Ser. No. 10/027,113, filed on Dec. 20, 2001 now U.S. Pat. No. 6,660,249, which is based on and claims priority of the Provisional application Ser. No. 60/258,423, filed on Dec. 27, 2000.

BACKGROUND OF THE INVENTION

1. Field of the Invention

The current invention concerns a novel, safe, nonirritating and physiologically compatible inhalable aztreonam formulation suitable for treatment of pulmonary bacterial infections caused by gram negative bacteria, such as *Escherichia coli, Enterobacteria* species, *Klebsiella pneumoniae, K. oxytoca, Proteus mirabilis, Pseudomonas aeruginosa, Serratia marcescens, Haemophilus influenzae, Burkholderia cepacia, Stenotrophomonas maltophilia, Alcaligenes xylosoxidans*. In particular, the invention concerns the inhalable formulation comprising aztreonam or a pharmaceutically acceptable salt thereof suitable for treatment and prophylaxis of acute and chronic pulmonary bacterial infections, particularly those caused by gram-negative bacteria *Burkholderia cepacia, Stenotrophomonas maltophilia, Alcaligenes xylosoxidans*, and multidrug resistant Pseudomonas aeruginosa which are resistant to treatment with other antibiotics. The inhalable formulation is delivered as an aerosol or as an inhalable dry powder. For aerosolization, about 1 to about 250 mg of aztreonam is dissolved in about 1 to about 5 ml of saline or other aqueous solution having a pH between 4.5 and 7.5, delivered to the lung endobronchial space in an aerosol having mass medium average diameter particles predominantly between 1 to 5μ using a nebulizer able to atomize the aztreonam solution into particles of required sizes. The aerosol formulation has a small volume yet delivers a therapeutically efficacious dose of aztreonam to the site of the infection in amounts sufficient to treat bacterial pulmonary infections. A combination of the novel formulation with the atomizing nebulizer permits about 50% delivery of the administered dose of aztreonam into airways. For delivery of dry inhalable powder, aztreonam is milled or spray dried to particle sizes between about 1 and 5μ. The dry powder formulation or a reconstituted aztreonam solid for aerosolization have a long shelf-life and storage stability.

2. Background and Related Disclosures

A wide variety of gram-negative bacteria cause severe pulmonary infections. Many of these bacteria are or become resistant to commonly used or specialty antibiotics and require treatment with new types of antibiotics. The pulmonary infections caused by gram-negative bacteria are particularly dangerous to patients who have decreased immunoprotective responses, such as for example cystic fibrosis and HIV patients, patients with bronchiectasis or those on mechanical ventilation.

Therefore, the bacterial respiratory infections caused by organisms resistant to antibiotics continues to be a major problem, particularly in immunocompromised or hospitalized patients, as well as in patients assisted by mechanical ventilation, as described in *Principles and Practice of Infectious Diseases*, Eds. Mandel, G. L., Bennett, J. E., and Dolin, R., Churchill Livingstone Inc., New York, N.Y., (1995).

Currently accepted therapy for severe bacterial respiratory tract infections, particularly for treatment of pneumonia in patients with underlying illnesses, includes treatment with various intravenous antibacterial agents, often used in two or three way combination. Most of these agents are not suitable, available or FDA approved for either oral or aerosol dosing. In some cases the efficacious systemic intravenous or oral dose, if oral delivery is possible, requires doses which are borderline or outright toxic thus often preventing a use of perfectly good antibiotic for treatment of the pulmonary infections.

Thus it would be desirable to have available other modes of delivery routes of these antibiotics enabling a targeted delivery of smaller amounts of the antibiotic to endobronchial space of airways for treatment of these bacterial infections rather than administering the antibiotic systemically in large amounts.

Additionally, chronically ill patients are often affected with infections caused by bacteria which are largely resistant to commonly used antibiotics or, upon extended use of certain antibiotic, often develop strong resistance to such antibiotic. For example, chronic pulmonary colonization with *Pseudomonas aeruginosa* in patients with cystic fibrosis is a principal cause of their high mortality. When established, the chronic pulmonary infection is very difficult, if not impossible, to eradicate. More than 60% of cystic fibrosis patients are colonized with *Pseudomonas aeruginosa* bacterium strains which are largely resistant to regular and specialty antibiotics, such as piperacillin, ticarcillin, meropenem, netilmicin and only little sensitive to azlocillin, ciprofloxacin, timentin and ceftazidime. Many strains have also been shown to develop resistance to tobramycin and to colistin, if used continuously.

Often, after prolonged antibiotic therapy, a superinfection with organisms intrinsically resistant to oral, intravenous or inhaled antibiotics develops in patients with cystic fibrosis and other chronic pulmonary infections. The four most common drug resistant organisms are *Burkholderia cepacia, Stenotrophomonas maltophilia, Alcaligenes xylosoxidans*, and multidrug resistant *Pseudomonas aeruginosa*.

Cystic fibrosis patients infected with *Burkholderia cepacia* have an increased rate of mortality compared to those patients with *Pseudomonas aeruginosa* infections. In some cystic fibrosis patients, *Burkholderia cepacia* can cause a rapid fatality, as described, for example in *Am. J. Respir. Crit. Care Med.*, 160:5, 1572–7 (1999).

The high level of antibiotic resistance demonstrated by most strains of *Burkholderia cepacia* severely limits therapeutic options for its treatment (*Clinics Chest Med.*, 19:473–86 (September 1998)). Furthermore, unlike *Pseudomonas aeruginosa, Burkholderia cepacia* can cause epidemic spread among cystic fibrosis patients and therefore any patient infected with *Burkholderia cepacia* is usually isolated from other patients. This causes both additional expenses connected with caring for these patients and may also be psychologically devastating to the patient. Furthermore, most lung transplant centers will not perform a lung transplant on patients infected with *Burkholderia cepacia* (*Clinics Chest Med.*, 19:473–86 (September 1998)). Therefore, the *Burkholderia cepacia* infection is often viewed as a death sentence by patients with cystic fibrosis.

*Burkholderia cepacia* is usually resistant to the parenteral delivery of various antibiotics, including aztreonam, with showing only 5% of isolates to be sensitive to such treatment (*Antimicrob. Agents Chemother.*, 34:3, 487–8 (March 1990)). Thus it would be advantageous to have available treatment for *Burkholderia cepacia* infections.

Other gram-negative bacteria intrinsically resistant to tobramycin can also complicate the care of a cystic fibrosis patient. These bacteria include *Stenotrophomonas maltophilia* and *Alcaligenes xylosoxidans*. Antibiotic therapy of these infections is usually also ineffective or leads to rapid emergence of drug resistance. Therefore, the successful treatment of all these infections requires that samples of these isolates are sent to a laboratory for complex antibiotic synergy determination of proper therapy for each individual patient (*Ped. Pulmon.*, S17:118–119 (1998)). It would, therefore, be also advantageous to provide a therapy for these rare but hard to treat bacterial infections.

Similarly, the development of *P. aeruginosa* infection with strains which are resistant to, that is which have a high minimal inhibitory concentration (MIC) to a majority of antibiotics including tobramycin, predicts declining lung function and also may disqualify the patient from consideration for lung transplant (*Clinics Chest Med.*, 19:535–554 (September 1998)).

Existing antibiotic treatments for *Burkholderia cepacia, Stenotrophomonas maltophilia, Alcaligenes xylosoxidans*, and multidrug resistant *Pseudomonas aeruginosa* pulmonary infections are either ineffective, or lead to rapid emergence of drug resistance.

From the brief description above, it is clear that there is a continuous need for an effective therapy for treatment of acute and chronic pulmonary bacterial infections caused by gram-negative bacteria and particularly those caused by *Burkholderia cepacia, Stenotrophomonas maltophilia, Alcaligenes xylosoxidans*, and multidrug resistant *Pseudomonas aeruginosa* lung infections. Such therapy would preferably comprise an inhalation of the aerosolized drug formulation delivering a therapeutically effective amount of the drug directly to the endobronchial space of airways to avoid systemic treatment.

The problems connected with infections caused with these antibiotic resistant bacteria are very serious and it would be advantageous to have available more efficient modes of treatments with different types of antibiotics.

Aztreonam is a synthetic antibiotic which has a good biological activity against gram-negative bacteria and it has previously been used for intravenous treatment of bacterial infections. However, its use is severely limited due to its low efficacy requiring administration of very large intravenous doses between 1000 and 4000 mg a day in order to treat the infections caused by gram-negative bacteria. Although it would be an antibiotic of choice for complementary treatment of patients treated with tobramycin or other antibiotics, particularly in cystic fibrosis patients, such treatment is not practical because of the high doses required.

Moreover, aztreonam is currently only available as an arginine salt. Arginine has been shown to be toxic to the lung and causes lung tissue irritation, inflammation, bronchospasm and cough and therefore is not suitable for a delivery by aerosolization. Consequently, aztreonam arginine salt is not approved for inhalation use in the United States or elsewhere.

However, as the antibiotic for treatment of pulmonary bacterial infections caused by gram negative bacteria, aztreonam could become a drug of choice for such treatment, if it could be delivered by inhalation in therapeutically effective concentrations directly to the lungs and if the problems connected with the aztreonam arginine can be overcome.

However, the efficacious administration of aztreonam by inhalation is further complicated by a lack of safe, physiologically acceptable and stable formulations for use by inhalation. Such formulation must meet several criteria, such as certain size range of inhalable particles, certain pH range and certain degree of salinity. When the aerosol contains a large number of particles with a mass medium average diameter (MMAD) larger than 5μ, these are deposited in the upper airways decreasing the amount of antibiotic delivered to the site of infection in the endobronchial space of airways. Similarly, both highly acidic and alkaline or hypotonic or hypertonic conditions lead to respiratory complications, such as bronchospasm and cough, preventing inhalation of the drug.

Thus it would be advantageous and desirable to provide an inhalable formulation for delivery of aztreonam by aerosol or a dry powder formulation for treatment of pulmonary gram-negative bacterial infections and particularly those caused by drug resistant strains *Burkholderia cepacia, Stenotrophomonas maltophilia, Alcaligenes xylosoxidans*, and multidrug resistant *Pseudomonas aeruginosa*, wherein the formulation comprises a smallest possible therapeutically effective amount of drug in a form which does not cause pulmonary inflammation, wherein the pH is adjusted to physiologically acceptable levels, wherein the aqueous solution is isotonic and wherein said formulation has adequate shelf life suitable for commercial distribution, storage and use.

It is, therefore, a primary object of this invention to provide a method for treatment of gram-negative infections, especially those caused by *Burkholderia cepacia, Stenotrophomonas maltophilia, Alcaligenes xylosoxidans*, and multidrug resistant Pseudomonas aeruginosa by providing a safe, physiologically acceptable and efficacious formulation for inhalation using a pure concentrated aztreonam free base, or a pharmaceutically acceptable salt thereof, which formulation contains sufficient but not excessive concentration of the active drug, which formulation can be efficiently aerosolized by nebulization using jet, ultrasonic or atomization nebulizers, into an aerosol having particle sizes within a range from 1 to 5μ, or administered as a dry powder, both well tolerated by cystic fibrosis patients and by patients with impaired pulmonary function due to infections, inflammation or another underlying disease.

All patents, patent applications and publications cited herein are hereby incorporated by reference.

SUMMARY

One aspect of this invention is a method for treatment of pulmonary infections caused by gram-negative bacteria.

Another aspect of this invention is a method for treatment of pulmonary bacterial infections caused by gram-negative bacteria, said method comprising administration of an inhalable concentrated pure aztreonam, or a pharmaceutically acceptable salt thereof, in a dry powder form or as an aerosol containing from about 1 to about 750 mg of aztreonam, or a pharmaceutically acceptable salt thereof, said aztreonam administered in an inhalable dry powder form or dissolved in from about 1 to about 5 ml of an aerosolable solution of pH between 4.5 and 7.5 containing from about 0.1 to about 0.9% of chloride or other anion to the lung endobronchial space of airways of a patient in need thereof by nebulization in an aerosol having a mass medium average diameter between about 1 and about 5μ.

Still another aspect of this invention is a method for treatment of pulmonary bacterial infections caused by gram-negative bacteria comprising administering a formulation of about 1 to about 250 mg of aztreonam once, twice, three times or four times a day up to a daily dose of aztreonam of 750 mg a day.

Yet another aspect of this invention is a method for treatment of pulmonary bacterial infections caused by *Escherichia coli, Enterobacteria* species, *Klebsiella pneumoniae, K. oxytoca, Proteus mirabilis, Pseudomonas aeruginosa, Serratia marcescens, Haemophilus influenzae, Burkholderia cepacia, Stenotrophomonas maltophilia, Alcaligenes xylosoxidans*, and multidrug resistant *Pseudomonas aeruginosa* using an inhalable formulation of aztreonam or a pharmaceutically acceptable salt thereof delivered by inhalation to the endobronchial space of airways in a dry powder form or in an aerosol.

Another aspect of this invention is an inhalable pharmaceutically acceptable composition comprising from about 1 to about 250 mg per one dose of aztreonam or a pharmaceutically acceptable salt thereof, said composition suitable for treatment of pulmonary bacterial infections caused by gram-negative bacteria wherein said aztreonam or the pharmaceutically acceptable salt thereof are prepared as an inhalable dry powder or as an aerosolable solution.

Still another aspect of this invention is an aerosolized aztreonam formulation comprising from about 1 to about 50 mg/ml of aztreonam or a pharmaceutically acceptable salt thereof dissolved in from about 1 to 5 ml of a normal or diluted saline or another aqueous solution, having pH between 4.5 and 7.5.

Still another aspect of the current invention is a formulation comprising from about 1 to about 250 mg of aztreonam in a diluted saline solution ranging from one tenth to a half normal saline or other aqueous solvent containing chloride or another anion, wherein said formulation has a pH between 5.5 and 7.0 and is delivered by aerosolization in about 1–5 ml of solution wherein aerosol has particles of the mass medium average diameter predominantly between 1 and 5μ, wherein said formulation is nebulized using a jet, atomizing, electronic or ultrasonic nebulizer.

Still yet another aspect of the current invention is a dry powder formulation comprising from about 1 to 200 mg of aztreonam or a pharmaceutically acceptable salt thereof, wherein said formulation is milled, spray dried or precipitated into a fine powder having particles with the mass medium average diameter between 1 and 5μ used for inhalation of the dry powder administered from one to four times per day not exceeding 750 mg per day.

Another aspect of this invention is a two-part reconstitution system comprising an aztreonam in dry or lyophilized powder form and a diluent stored separately until use.

Definitions:

As used herein:

"MMAD" means mass medium average diameter.

"Normal saline" means water solution containing 0.9% (w/v) NaCl.

"Diluted saline" means normal saline containing 0.9% (w/v) NaCl diluted into its lesser strength from about 0.1% to about 0.8%.

"Half normal saline" or "½ NS" means normal saline diluted to its half strength containing 0.45% (w/v) NaCl.

"Quarter normal saline" or "¼ NS" means normal saline diluted to its quarter strength containing 0.225% (w/v) NaCl.

"One tenth normal saline" or "1/10 NS" means normal saline diluted to its one tenth strength containing 0.09% (w/v) NaCl.

"CF" means cystic fibrosis.

"Predominantly" means including at least 70% but preferably 90% of particle sizes between 1 and 5μ.

"Physiologically acceptable solution" means a saline diluted to between 1/10 NS or 1 NS or another aqueous solution comprising from about 31 to about 154 mM of chloride or an equivalent concentration of bromine or iodine.

"Composition" means an aztreonam containing formulation additionally containing other components, such as excipients, diluents, isotonic solutions, buffers, etc.

"Formulation" means a specific composition formulated for specific use, such as for aerosolization of aztreonam containing solution or nebulization of dry powder.

"Aztreonam composition" or "aztreonam formulation" means a composition or formulation comprising an indicated amount of aztreonam free base or the equivalent of that amount in an aztreonam salt. Thus, if for example, the dose of aztreonam comprises molar amount of aztreonam free base, the aztreonam salt comprises equal molar amount of salt.

"Concentrated aztreonam" means an aztreonam concentrated into a form which permits dilution of more than 83.3 mg of aztreonam free base in 1 ml of diluent.

DETAILED DESCRIPTION OF THE INVENTION

The current invention concerns a discovery that specifically formulated and delivered inhalable aztreonam or a pharmaceutically acceptable salt thereof is efficacious for treatment of pulmonary infections caused by gram-negative bacteria.

Consequently, the invention concerns an inhalable composition and a method of treatment for pulmonary bacterial infections caused by *Escherichia coli, Enterobacter* species, *Klebsiella pneumoniae, Klebsiella oxytoca, Proteus mirabilis, Pseudomonas aeruginosa, Serratia marcescens, Haemophilus influenzae*, including ampicillin-resistant and other penicillinases-producing strains and *Nitrobacter* species as well as for treatment of more rare bacteria, such as *Burkholderia cepacia, Stenotrophomonas maltophilia, Alcaligenes xylosoxidans*, and multidrug resistant *Pseudomonas aeruginosa*. The aztreonam formulation or a formulation comprising a pharmaceutically acceptable salt thereof is delivered to a patient's endobronchial space of airways by inhalation of a dry powder or an aerosol solution.

The method of treatment of pulmonary bacterial infections is especially suitable for treatment of patients with cystic fibrosis, bronchiectasis and patients with pneumonia assisted by ventilators, however it is also useful for treatment of other conditions that are complicated by infections caused by *Burkholderia cepacia, Stenotrophomonas maltophilia, Alcaligenes xylosoxidans*, and multidrug resistant *Pseudomonas aeruginosa* or other gram-negative bacteria.

The current invention thus concerns a novel, efficacious, safe, nonirritating and physiologically compatible inhalable aztreonam composition suitable for treatment of pulmonary bacterial infections caused by gram-negative bacteria particularly those which are resistant to treatment with other antibiotics. The inhalable formulation of aztreonam or a pharmaceutically acceptable salt thereof is suitable both for treatment and prophylaxis of acute and chronic pulmonary infections. The inhalable formulation is delivered as an aerosol or as an inhalable dry powder. For aerosolization, aztreonam is dissolved in a minimal volume of about 1 to about 5 ml of an aqueous solvent comprising chloride bromine or iodine ion, having a pH between 4.5 and 7.5, delivered to the endobronchial space in an aerosol having mass medium average diameter particles predominantly between 1 to 5μ using a nebulizer able to aerosolize the aztreonam solution into particles of required sizes.

I. Aztreonam and Pharmaceutically Acceptable Salts Thereof

Aztreonam is a known synthetic monocyclic monobactam antibiotic with antibacterial activity against most gram-negative bacteria. Aztreonam arginine salt, known under its trade name AZACTAM® is currently FDA approved only for intravenous and intramuscular use.

A. Aztreonam Compound (I)

Aztreonam chemical formula is (Z)-2-[[[(2-amino-4-thiazolyl) [[ (2S,3S)-2-methyl-4-oxo-1-sulfo-3-azetidinyl] carbamoyl]methylene] amino] oxy]-2-methylpropionic acid.

Aztreonam is a moncbactam and as such it has a unique monocyclic beta-lactam nucleus, and is therefore structurally different from other β-lactam antibiotics such as, for example penicillins, cephalosporins, or cephamycins.

The sulfonic acid substituent in the 1-position of the ring activates the beta-lactam moiety. An aminothiazolyl oxime side chain in the 3-position and a methyl group in the 4-position confer the specific antibacterial spectrum and beta-lactamase stability.

AZACTAM® (aztreonam for injection, USP) commercially available from DURA Pharmaceuticals, Inc., San Diego, Calif., contains aztreonam as the active ingredient. AZACTAM® is supplied as a sterile, nonpyrogenic, sodium-free, white to yellowish-white lyophilized powder containing arginine. AZACTAM is formulated for intramuscular or intravenous use. (PDR, pg. 1159 (2001)).

The commercially available AZACTAM intravenous or intramuscular formulation is not suitable for inhalable use because of the presence of arginine in the formulation. Arginine has been found to cause pulmonary inflammation when administered in aerosol form to the lung in the rat.

Arginine has been unsuccessfully used as a potential aerosolized mucolytic agent in cystic fibrosis patients. A study, described in *Pediatrics*, 55:96–100 (1975) recommends that arginine should not be used in cystic fibrosis patients. In a study of 24 patients with cystic fibrosis, inhalation therapy with an arginine solution in five patients had to be stopped because of severe deterioration of their general conditions and the appearance of cough. The presence of airway inflammation in these five patients was confirmed by bronchoscopy. Since than, it has been discovered that arginine is a substrate for the production of nitric oxide radicals.

Nitric oxide radical reacts with the superoxide anion to form peronitrile, which is by itself toxic to the tissue and also may further react to form highly reactive and toxic hydroxyl radical. Since inflammation is a serious impairment for cystic fibrosis and all other diseases which this invention attempts to treat, use of arginine salt would defeat this purpose as it would worsen rather than better the patient conditions.

Arginine is also an important substrate for immune complex injury in the lung, as disclosed in *PNAS*, 14:6338–6342 (1991). Since the aerosolization concentrates high levels of the aerosolized drug in the lung as compared to dilution seen after intravenous administration, the aerosolization of the aztreonam arginine salt would be detrimental rather than advantageous treatment for cystic fibrosis patients or patients suffering from pulmonary infections. Moreover, it would dilute and/or negate the effect of aztreonam.

Aztreonam is not currently approved or used for inhalation treatment and aerosol administration in the United States. Consequently, there is no known aztreonam containing formulation available for aerosol delivery of aztreonam to the endobronchial space of airways. The only attempt to deliver aztreonam intermittently to cystic fibrosis subjects is described in *Spanish Annals on Pediatrics*, 40: No.3 (1994) where such delivery was made in an open label trial in cystic fibrosis patients with intermittently administered 500 and 1000 mg of AZACTAM USP arginine salt, twice a day for 21 days, using CR60 System 22 unit nebulizer. The intent of this study was to treat aztreonam sensitive *Pseudomonas aeruginosa* organisms, but not multidrug resistant *Pseudomonas aeruginosa*. No effort or speculation was to treat *Burkholderia cepacia*, *Stenotrophomonas maltophilia*, infections caused by *Alcaligenes xylosoxidans* or other gram-negative bacteria.

In this study, the nebulized solution of aztreonam was delivered after the physical therapy session. Prior to the therapy session, the patients were administered 3cc of saline alone or mixed with bronchodilators salbutamol or ipratropium bromide and fenoterol bromohidrate to prevent bronchospasm. The treatment described in this study thus required both the pretreatment with inhaled saline and/or bronchodilating agents and prior physical therapy session as well as administration of large doses of the drug to be administered twice a day. Although in about 80% of patients lung function has somehow improved, such improvement was not statistically significant. At least one patient could not tolerate the therapy due to bronchospasm. Most patients required administration of bronchodilators and all patients underwent physical therapy prior to aztreonam treatment in order to tolerate the administration of large doses of nebulized aztreonam. Aztreonam therapy was discontinued if in vitro resistance was found. One patient developed *Burkholderia cepacia*, which was viewed as superinfection, and a possible adverse outcome. The reference, although suggestive of efficacy in drug sensitive *Pseudomonas aeruginosa*, which is expected because the drug is known for its effect on the gram-negative bacteria, does not disclose the use of low doses of aztreonam, or its continuous use, or the use of aztreonam salts which do not cause bronchospasm, or the use of aztreonam for treatment of multidrug resistant *P. aeruginosa* and teaches away from use in *Burkholderia cepacia*, *Stenotrophomonas maltophilia*, *Alcaligenes xylosoxidans*, and multidrug resistant *Pseudomonas aeruginosa*. Furthermore, the high incidence of bronchospasm developed with use of the disclosed formula requiring either discontinuation or pretreatment with bronchodilators indicates the need for a different formulation safe for inhalation use.

B. Aztreonam Biological and Pharmacological Activity

Aztreonam exhibits potent and specific activity in vitro against a wide spectrum of gram-negative aerobic pathogens including *Pseudomonas aeruginosa*. The bactericidal action of aztreonam results from the inhibition of bacterial cell wall synthesis due to a high affinity of aztreonam for penicillin binding protein 3 (PBP3).

Aztreonam, unlike the majority of β-lactam antibiotics, does not induce β-lactamase activity and its molecular structure confers a high degree of resistance to hydrolysis by β-lactamases, such as penicillinases and cephalosporinases, produced by most gram-negative and gram-positive pathogens. Aztreonam is therefore especially active against gram-negative aerobic organisms that are resistant to antibiotics hydrolyzed by β-lactamases.

Aztreonam maintains its antimicrobial activity at a pH ranging from 6 to 8 in vitro (AZACTAM® product label, Dura Pharmaceuticals), as well as in the presence of human serum and under anaerobic conditions. Aztreonam is active in vitro and is effective in laboratory animal models and clinical infections against most strains of the following organisms, *Escherichia coli, Enterobacter species, Klebsiella pneumoniae, Klebsiella oxytoca, Proteus mirabilis, Pseudomonas aeruginosa, Serratia marcescens, Haemophilus influenzae*, and *Nitrobacter* species, including many that are multi-resistant to other antibiotics such as certain cephalosporins, penicillins, and aminoglycosides.

Aztreonam is thus suitable for treatment of infections caused by *Escherichia coli, Enterobacter species, Klebsiella pneumoniae, Klebsiella oxytoca, Proteus mirabilis, Pseudomonas aeruginosa, Serratia marcescens, Haemophilus influenzae, Nitrobacter* species.

Currently, the only infections for which AZACTAM is FDA approved are those caused by *Escherichia coli, Klebsiella pneumoniae, Pseudomonas aeruginosa, Haemophilus influenzae, Proteus mirabilis, Enterobacter* species and *Serratia marcescens*.

It has now been found that all the above named bacterial strains as well as rare and very resistant strains, such as *Burkholderia cepacia, Stenotrophomonas maltophilia, Alcaligenes xylosoxidans*, and multidrug resistant *Pseudomonas aeruginosa* are successfully eradicated by daily treatment with low doses between about 1 and about 250 mg of aztreonam free base or a pharmaceutically acceptable salt thereof, preferably administered once or twice a day, with total daily doses not exceeding 750 mg/day.

II. Aztreonam Pharmacologically Acceptable Salts

Currently, the only commercially available salt of aztreonam is arginine. As already discussed above, the aztreonam salt is not suitable for inhalation administration because arginine, after aerosol exposure, is known to cause pulmonary inflammation, bronchospasm and cough. AZACTAM, aztreonam containing arginine salt, is not approved by regulatory authorities for inhalation use. Therefore, other aztreonam salts are needed to achieve a safe formulation of aztreonam for inhalation treatment of patients with pulmonary infections or those having impaired pulmonary function due to cystic fibrosis or bronchiectasis.

Since the aztreonam containing arginine is not suitable for inhalation according to this invention, other acid addition salts were precared according to Example 3, tested and found pharmacologically acceptable and without detrimental secondary effects when administered as a dry powder or aerosol.

The aztreonam for use in the current invention is prepared in the form of salts derived from inorganic or organic acids. These salts include but are not limited to the following salts: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethane-sulfonate, lactate, maleate, methanesulfonate, nicotinate, 2-napthalenesulfonate, oxalate, pamoate, pectinate, persulfate, 3-phenylpropionate, picrate, pivalate, propionate, succinate, tartrate, thiocyanate, p-toluenesulfonate and undecanoate.

Examples of acids which may be employed to form pharmaceutically acceptable acid addition salts include such inorganic acids as hydrochloric acid, sulphuric acid and phosphoric acid and such organic acids as, for example, oxalic acid, maleic acid, acetic, aspartic, succinic acid and citric acid. Basic addition salts can be prepared in situ during the final isolation and purification of the compound of formula (I), or separately by reacting the carboxylic or sulfuric acid function with a suitable base such as the hydroxide, carbonate or bicarbonate of a pharmaceutically acceptable metal cation or with ammonia, or with an organic primary, secondary or tertiary amine.

Pharmaceutical acceptable salts also include, but are not limited to, cations based on the alkali and alkaline earth metals, such as sodium, lithium, potassium, calcium, magnesium or aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, amino acids including basic amino acids (i.e. lysine, histidine, ornithine) and the like. Other representative organic amines useful for the formation of base addition salts include diethylamine, ethylenediamine, ethanolamine, diethylamine and the like.

Any of the above named salt may be delivered as a single salt or as admixture of one or several salts as long as the equivalent amount of aztreonam is within 1 to 250 mg per one dosage.

The preferred pharmaceutically acceptable aztreonam salt is derived from reaction of aztreonam with hydrochloric acid, hydrobromic acid, sulfuric acid, nitric acid and phosphoric acid as these salts are not known to cause pulmonary inflammation and are safer than arginine salts.

III. Aztreonam Inhalable Composition

The current invention primarily concerns a concentrated inhalable aztreonam composition suitable for efficacious delivery of aztreonam or the aztreonam pharmaceutically acceptable salt into the endobronchial space of airways by aerosolization or as a dry powder.

The invention is most preferably suitable for formulation of concentrated aztreonam for aerosolization by atomizing, jet, ultrasonic, pressurized, vibrating porous plate or equivalent nebulizers or by dry powder inhalers which predominantly produce aztreonam aerosol or dry powder particles between 1 and 5μ. Such particle sizes are necessary for efficacious delivery of aztreonam into the endobronchial space to treat bacterial infections.

A. Aerosolized Aztreonam Composition

Aztreonam composition for aerosolization is formulated for efficacious delivery of aerosolized aztreonam to the lung endobronchial space of airways.

The aerosol formulation is delivered in a total volume of between about 1 and about 5 ml of aqueous physiologically acceptable solution for one inhalation dose. When formulated and delivered according to the method of invention, it delivers a therapeutically efficacious dose of aztreonam to the site of the infection in amount of aztreonam sufficient to treat bacterial pulmonary infections.

A combination of the novel aqueous formulation with the atomizing, jet, pressurized, vibrating porous plate or ultrasonic nebulizer permits, depending on the nebulizer, about at least 20 to about 90%, typically about 70% delivery of the administered dose of aztreonam into airways.

The formulation contains a minimal yet efficacious amount of aztreonam from 1 to about 250 mg formulated in the smallest possible volume of physiologically acceptable diluent having a certain degree of salinity and certain pH, adjusted to permit generation of an aztreonam aerosol well tolerated by patients but minimizing the development of secondary undesirable side effects such as bronchospasm and cough.

Primary requirements for aerosolized aztreonam formulation are its safety and efficacy. Additional advantages are lower cost, practicality of use, long shelf-life, storage and manipulation of the aerosol device. These requirements for aerosolized aztreonam have now been found to be met by the formulation containing certain degree of salinity and have certain pH range.

1. Dosage of Aztreonam or Salt Thereof

Aztreonam has relatively short life-time. Consequently, the effective treatment of bacterial pulmonary infections requires a treatment regimen which provides sufficient amount of drug to maintain the antibacterial level of aztreonam in the lung. Such regimen thus requires administration of an inhalable aztreonam one to several, preferably two to four, times a day. Most preferred dosing regimen for patient convenience is once or twice a day, however, because of a specific effect aztreonam asserts on the bacteria, and because of its relatively short life-time of about 12 hours, more than twice a day dosing is often required for complete eradication of the bacteria from the endobronchial space.

It is therefore preferable to deliver aerosolized or dry powder aztreonam or a pharmaceutically acceptable salt thereof in the smallest therapeutically efficacious amount at least twice a day, in some instances three to four times, and exceptionally more than four times a day. A dose of aztreonam or a salt thereof is therefor set to be between 1 and 250 mg per one dose. Typically, one therapeutically effective dose contains between 1 and 250 mg of aztreonam free base or the salt thereof, in equivalent. Typically, the formulation and the nebulizer are selected to provide at least about 50%–70% efficacy of aztreonam delivery to the endobronchial space. Thus, with about a 250 mg dose, 125 mg of aztreonam is delivered during each administration. 100–250 mg of aztreonam delivered to the lung has been found to be efficacious in eradication of bacteria. In no instance should one dose exceed 250 mg. Above this amount, aerosolization is difficult, the drug tends to precipitate, and larger volumes are necessary for its delivery by aerosol, which defeats the purpose of the invention to deliver the therapeutical amount of drug with the greatest efficiency.

Determination of effective dosage of administered aztreonam and the regimen used for treatment of each patient depends on the responsiveness of the individual patient to the treatment. The ultimate decisive factor is the expected level of aztreonam in the sputum after aerosolization. The optimal range of aztreonam in 1 ml of sputum at any given time should be in the 500 to 2000 μg/mL range. Thus, the frequency of the administration is correlated with the effectiveness of administered aztreonam.

The effectiveness of aerosolized aztreonam is surprisingly high when compared to effectiveness of the intravenously administered aztreonam where the serum peak levels following the maximum permitted dose 2,000 mg resulted only in 242 ug/mL of sputum. Following such intravenous administration, the 6 hours levels were found to be in the range of 16 ug/ml, which is the MIC for non-resistant *Pseudomonas aeruginosa*.

The new mode of administration permitting a noninvasive administration of small yet effective amounts of aztreonam directly into lungs is great improvement compared to all previously known method used for delivery of aztreonam.

2. Effect of pH on Aztreonam Aerosol Formulation

The solution or diluent used for preparation of aztreonam aerosol has a limited pH range from 4.5 to 7.5, preferably between 5.5 and 7.0.

The pH of the formulation is an important feature for aerosolized aztreonam delivery. When the aerosol is either acidic or basic, it can cause bronchospasm and cough. Although the safe range of pH is relative and some patients may tolerate a mildly acidic aerosol, others, particularly those with cystic fibrosis or other underlying disease will experience bronchospasm. Any aerosol with a pH of less than 4.5 typically induces bronchospasm. Aerosols with a pH between 4.5 and 5.5 will cause bronchospasm occasionally. Testing with aztreonam aerosol discovered that an aerosolizable aztreonam formulation having a pH between 5.5 and 7.0 is well tolerated and safe. Any aerosol having pH greater than 7.5 is to be avoided as the body tissues are unable to buffer alkaline aerosols. Aerosol with controlled pH below 4.5 and over 7.5 result in lung irritation accompanied by severe bronchospasm cough and inflammatory reactions.

For these reasons as well as for the avoidance of bronchospasm, cough or inflammation in patients, the optimum pH for the aerosol formulation was determined to be between pH 5.5 to pH 7.0.

Consequently the aztreonam aerosol formulation is adjusted to pH between 4.5 and 7.5 with preferred pH range from about 5.5 to 7.0. Most preferred pH range is from 5.5 to 6.5.

3. Effect of Salinity on the Aztreonam Formulation

Patients suffering from acute or chronic endobronchial infections and particularly those with cystic fibrosis or bronchiectasis have increased sensitivity to various chemical agents and have high incidence of bronchospastic, asthmatic or cough incidents. Their airways are particularly sensitive to hypotonic or hypertonic and acidic or alkaline conditions and to the presence of any permanent ion, such as chloride. Any imbalance in these conditions or a presence of chloride above certain value leads to bronchospastic or inflammatory events and/or cough which greatly impair treatment with inhalable formulations. Both these conditions prevent efficient delivery of aerosolized aztreonam into the endobronchial space. The clinical manifestations of the irritated airways are extremely undesirable.

Clearly, for aztreonam, it is not possible to use solely an aqueous solvent without providing certain degree of osmolality to meet and emulate physiological conditions found in healthy lungs. Consequently, certain amount of the chloride or another anion is needed for successful and efficacious delivery of aerosolized aztreonam but such amount is much lower than amounts provided and typically used for aerosols of other compounds.

Bronchospasm or cough reflexes do not respond to the same osmolality of the diluent for aerosolization, however, they can be sufficiently controlled and/or suppressed when the osmolality of the diluent is in a certain range. Preferred solution for nebulization of aztreonam which is safe and has airways tolerance has a total osmolality between 50 and 550 mOsm/kg with a range of chloride concentration of between 31 mM and 300 mM. The given osmolality controls bronchospasm, the chloride concentration, as a permeant anion, controls cough. In this regard the chloride anion can be substituted with bromine or iodine anions, since both are permeant anions. In addition, bicarbonate may be wholly or partially substituted for chloride ion. Normal saline (NS) contains 154 mM of chloride whereas 31 mM of chloride corresponds to about 0.2 normal saline.

Consequently, the formulation for aztreonam aerosol of the invention comprises from about 1 to about 50 mg, preferably about 10 mg, of aztreonam dissolved in 1 ml of a normal, or preferably a diluted saline to from about 1/10 normal saline (NS) to about and at most to 1 NS solution, preferably from about 1/10 to about 1/4 NS, that is a one tenth to one quarter diluted normal saline. It has now been discovered that aztreonam is efficaciously delivered into lungs when dissolved in lesser than normal saline, that is saline containing 0.9% of sodium chloride, and that the concentration of a chloride ion equal to or lesser than 1/4 N saline permits and assures a delivery of aztreonam into endobronchial space.

The aztreonam formulation containing about 50 mg of aztreonam per 1 ml of 0.2 NS has an osmolality of about 290 mOsm/l. Such osmolality is within a safe range of aerosols suitable for administration to patients suffering from pulmonary bacterial infections and also those patients with a cystic fibrosis or bronchiectasis.

An additional feature and advantage of using 1/10 to 1/4 NS solution comprising 50 mg/ml aztreonam is that the resulting aerosol formulation is very efficiently nebulized by an atomic, jet or ultrasonic nebulizer compared to aztreonam dissolved in a normal saline. Since the delivery of aztreonam formulated as described herein is much more efficient, much lower amount of aztreonam is needed to achieve complete eradication of gram-negative bacteria in lungs. Instead of 1000 to 4000 mg of aztreonam which was shown to be somehow effective in the only one prior attempt to aerosolize aztreonam, the formulation of aztreonam according to this invention permits treatments with as little as 1 mg/ml and with at most up to 50 mg/ml of aztreonam in a maximum amount of 5 ml volume, delivered preferable with an atomizing, jet, electronic or ultrasonic nebulizer.

4. Preferred Aerosolizable Aztreonam Formulation

The aztreonam aerosolizable formulation comprises aztreonam or a pharmaceutically acceptable salt thereof in amount about 1 to about 50 mg/ml of about 1 to 5 ml of an aqueous solution containing low concentration of chloride ion, having pH adjusted to between 4.5 and 7.5, said formulation delivered by aerosolization using an atomizing, jet, electronic, ultrasonic nebulizer.

The preferred formulation of the current invention is a formulation comprising from about 10 to about 50 mg of aztreonam dissolved in about 1–5 ml of a saline diluted preferably to a quarter or one tenth strength of normal saline, having pH adjusted to between 5.5 and 7.0, delivered by nebulization in aerosol particles having the mass medium average diameter predominantly between 1 and 5μ, wherein said formulation is nebulized using an atomizing, jet, electronic or ultrasonic nebulizer.

The formulation according to the invention contains aztreonam formulated as a dry powder, aerosol solution or aerosol suspension of liposomes or other microscopic particles in an aqueous solvent. The formulation is designed to be well tolerated and able to be reliably and completely nebulized to aerosol particles within the respirable size range of 1 to 5μ.

The doses are designed to contain as much as, but not more than, the necessary amount of a most active form of aztreonam to prevent colonization and/or to treat severe pulmonary infections caused by a range of susceptible gram-negative organisms.

Patients can be sensitive to pH, osmolality, and ionic content of a nebulized solution. Therefore these parameters are adjusted to be compatible with aztreonam chemistry and still tolerable to patients.

The formulation of the invention is nebulized predominantly into particle sizes allowing a delivery of the drug into the terminal and respiratory bronchioles where the bacteria reside during infection and in the larger airways during colonization.

For efficacious delivery of aztreonam to the lung endobronchial space of airways in an aerosol particle, the formation of an aerosol having a mass medium average diameter predominantly between 1 to 5μ is necessary. The formulated and delivered amount of aztreonam for treatment and prophylaxis of endobronchial bacterial infections must effectively target the lung surface. The formulation must have a smallest possible aerosolizable volume able to deliver an effective dose of aztreonam to the site of the infection. The formulation must additionally provide conditions which would not adversely affect the functionality of the airways. Consequently, the formulation must contain enough of the drug formulated under the conditions which allow its efficacious delivery while avoiding undesirable reactions. The new formulation according to the invention meets all these requirements.

B. Aztreonam Dry Powder Composition

An alternative way to deliver inhalable aztreonam is by way of dry inhalable powder.

The aztreonam antibiotic compounds of the invention may be endobronchially administered in a dry powder formulation for efficacious delivery of the finely milled antibiotic into the endobronchial space using dry powder or metered dose inhalers as an alternative to aerosol delivery.

A dry powder formulation has potency, on a mass basis, which allows such alternative delivery of aztreonam as a dry powder using dry powder inhalers. A sufficiently potent formulation of aztreonam, or a pharmaceutically acceptable salt thereof, provides a dry powder which can be advantageously delivered by dry powder inhaler or by metered dose inhaler. For delivery of dry inhalable powder, aztreonam is milled, precipitated, spray dried or otherwise processed to particle sizes between about 1 and 5μ.

Dry powder formulation comprises from about 20 to 200 mg, preferably 10 to 100 mg of aztreonam or a pharmaceutically acceptable salt thereof.

For dry powder formulation of the invention, aztreonam, or a pharmaceutically acceptable salt thereof, is milled to a powder having mass median average diameters ranging from 1–5 microns by media milling, jet milling, spray drying or particle precipitation techniques.

Particle size determinations are made using a multi-stage Anderson cascade impactor or other suitable method. The Thermo Andersen Eight Stage Non-Viable Cascade Impactor is specifically cited within the US Pharmacopoeia Chapter 601 as a characterizing device for aerosols within metered-dose and dry powder inhalers. The Eight Stage Cascade Impactor utilizes eight jet stages enabling classification of aerosols from 9.0 micrometers to 0.4 micrometers (at 28.3 L/min) and allows airborne particulate to imp act upon stainless steel impaction surfaces or a variety of filtration media substrates. A final filter collects all particles smaller than 0.4.

Media milling is accomplished by placing a drug substance into a mill containing, for example, stainless steel or ceramic balls and rotating or tumbling the material until the desired drug particle size ranges are achieved. Advantages of media milling include good size control, narrow product size ranges, high efficiencies or recovery, and readily scalable processes. Disadvantages include long manufacturing process times which takes from several hours to several days, the requirement that the milling media be separated from the product at completion, and the possibility of contamination of the product with the media.

Jet milling uses very high pressure air streams to collide particles with one another, with fine particles of the desired size being recovered from the mill. Advantages include rapidity of the manufacturing process and less energy transfer during milling, resulting in less temperature rise during the drug production. The jet milling process is completed in seconds to minutes. Disadvantages of the jet milling include poorer yield and collection efficiencies, with only 50 to 80% of recovery being a typical yield.

Spray-drying is another technique useful for preparation of inhalable dry powder. Spray drying involves spraying a fine mist of aztreonam solution onto a support and drying the particles. The particles are then collected. Spray drying has the advantage of being the least prone to degrading chemical entities. Adding a co-solvent which decreases the solubility of a drug to a uniform drug solution results in solution precipitation. When sufficient co-solvent is added, the solubility of the drug falls to the point where solid drug particles are formed which can be collected by filtration or centrifugation. Precipitation has the advantage of being highly reproducible, having a high yield of recovery and being able to be performed under low temperature conditions, which reduce degradation.

Dry powder inhalation and metered dose inhalations are more practical when administered doses result in the delivery of at least about 10 mg, and more preferably about 25 to about 100 mg, of aztreonam antibiotic compound to the lung of the patient receiving treatment. Depending on the efficiency of the dry powder delivery device, which is typically about 70%, typical effective dry powder dosage levels fall in the range of about 20 to about 60 mg of aztreonam. Therefore, typically more than one breath of drug is required.

In this aspect, the invention provides a sufficiently potent formulation of pure aztreonam antibiotic or a pharmaceutically acceptable salt in dry powder or metered dose form of drug particles milled or otherwise prepared to particle sizes predominantly with a range of 1 to 5 microns. Such formulation is practical and convenient because it does not require any further handling such as diluting the dry powder or filling an aerosol container. Further, it utilizes the devices that are sufficiently small, fully portable and do not require, for example, an air compressor which is needed for a jet nebulizer. Additionally, the dry powder formulation has a longer shelf life that the liquid aztreonam formulations for aerosolization. Aztreonam, when reconstituted into an aerosolizable solution, has only a limited shelf life at room temperature due to hydrolysis of the monobactam ring. Aztreonam dry powder does not have this problem.

The dry powder formulation is thus practical and convenient for ambulatory use because it does not require dilution or other handling, it has an extended shelf-life and storage stability and the dry powder inhalation delivery devices are portable and do not require an air compressor needed by aerosol nebulizers.

All techniques suitable for preparation of dry inhalable powders and any and all improvements thereof as well as any dry powder inhaler are intended to be within the scope of the invention.

C. Shelf-Life and Storage

Stability of the formulation is another very important issue for efficacious formulation. If the drug is degraded before aerosolization, a smaller amount of the drug is delivered to the lung thus impairing the treatment efficacy. Moreover, degradation of stored aztreonam may generate materials that are poorly tolerated by patients.

The dry form of aztreonam has at least 2 years long shelf life. The liquid forms of the arginine/aztreonam free base have a 24-hour stability at room temperature, 48 hours when refrigerated, and when frozen at −4° C., such stability can be extended to about three months. However, the stability of aztreonam arginine salt is an attribute of arginine. The stability of other salts, after liquid reconstitution may differ.

A long-term stability of aztreonam free base or aztreonam salt in aqueous solutions may not provide a sufficiently long shelf life which would be commercially acceptable. A liquid formulation, therefore, may require a separation of aztreonam or aztreonam salt from the appropriate diluent. For this reason, the formulation is preferably supplied in a dry form and can be a reconstituted prior to administration.

A formulation for aerosolization is thus preferably provided as two separate components, one containing a dry aztreonam or a salt thereof and a second containing an appropriate diluent such as 0.1 to 0.9 N saline, bicarbonate or any equivalent acqueous solution, as described above. The formulation is reconstituted immediately prior to administration. This arrangement prevents problems connected with the long-term stability of aztreonam in aqueous solvents.

According to the invention, aztreonam for aerosolization is preferably formulated in a lyophilized dosage form intended for use as a dry powder for reconstitution before inhalation therapy. The formulation of aztreonam can be aseptically prepared as a lyophilized powder either for dry powder delivery or for reconstitution and delivery, or as a frozen solution, a liposomal suspension, or as microscopic particles. The storage suitability of the formulation allows reliable reconstitution of the formulated aztreonam suitable for aerosolization.

IV. Administration of Aztreonam by Inhalation

Aztreonam is currently only available for parenteral use in the form of the arginine salt. Arginine is known to cause pulmonary inflammation and irritation, as discussed above, and is, therefore, unsuitable for inhalation use.

A. Two Modes of Inhalable Administration

Administration of inhalable aztreonam is achieved either with aztreonam aerosol or with inhalable dry aztreonam powder.

An arginine free formulation according to the invention delivered by inhalation, however, has been shown to safely treat respiratory infections caused by all susceptible gram-negative bacteria including Pseudomonas aeruginosa, *Escherichia coli, Klebsiella pneumoniae, Pseudomonas aeruginosa, Haemophilus influenzae, Proteus mirabilis, Enterobacter* species and *Serratia marcescens*, as well as, and more importantly, antibiotics resistant strains *Burkholderia cepacia, Stenotrophomonas maltophilia, Alcaligenes xylosoxidans*, and multidrug resistant *Pseudomonas aeruginosa*.

B. Frequency of Dosing

The frequency of dosing is another aspect of this invention. Treatment of pulmonary infections caused by the above named bacteria is achieved by a treatment regimen which provides one to several, preferably four, times a day an inhalable aztreonam. Most preferred dosing regimen for patient covenience is once or twice a day, however, because of a specific effect aztreonam asserts on the bacteria, and because of its relatively short life-time of about 12 hours, more often dosing is often required for complete eradication of the bacteria from the endobronchial space.

In patients with severely impaired lung function, the frequency of dosing may be increased up to about twelve times a day each time, providing only such amount of aztreonam as necessary to maintain therapeutic level in the lung.

Aztreonam kills bacteria by lysing cell walls as long as the local concentration of antibiotic exceeds the bacteria minimal inhibitory concentration (*Med. Clinics N. Am.*, 79:4, 733:743 (1995)). Because of the relatively rapid clearance of antibiotics from the respiratory tract due to mucociliary action, greater efficacy is obtained at a lower dose of administered aztreonam by treating a patient three, four or more times a day rather than administer the drug only once or twice. To this effect the dose delivered by inhalation is at least four times and can be one thousand time lower then the dose delivered intravenously or utilized in the one attempt described above to deliver aztreonam by aerosolization where 500–1000 mg was delivered twice a day to a total amount of 1000 mg for children under 5 years of age and 2000 mg for individuals older than 5 years.

The current daily dose can be as small as 2 mg. The typical upper limit is 500 mg of aztreonam per day delivered in two to four administrations. In extreme cases the dose may reach up to 750 per day delivered in three, four or more aerosol administrations. Typical and preferred range for one aerosol dosage is between 20 and 200 mg administered twice a day or between 10 and 100 mg administered three or four times per day. For dry powder inhalation, the dose for one administration is lower, typically between about 10 and 100 mg per one dose and at maximum can reach 200 mg per one dose.

Aerosolization of aztreonam utilizes delivery of aerosolized aztreonam or a pharmaceutically acceptable salt thereof, or a mixture of salts using atomizing, jet, ultrasonic; electronic or other equivalent nebulizers. Those which are portable, such as atomizing, ultrasonic and electronic nebulizers are preferred for ambulatory treatment. The jet nebulizers with a compressor nebulize the aztreonam formulation very efficiently but are more suitable for use in the hospital and doctor's office.

A dry powder inhalation, as the second mode of administration of the inhalable aztreonam, also utilizes the aztreonam, or a pharmaceutically acceptable salt or a mixture thereof, but aztreonam is formulated as an aztreonam dry powder formulation. Such formulation comprises a delivery of the finely milled aztreonam directly to the endobronchial space. In this instance, aztreonam is delivered into the endobronchial space using dry powder or metered dose inhalers. The aztreonam potency, determined on a mass basis, allows the inhalation of aztreonam powder, as an alternative mode of administration to the aerosol. Dry powder inhalation is most efficacious, practical and economical when administered doses contain less than 100 mg. The frequency of dosing, thus, is typically three or four times a day but also includes one or two or more than four times dosing regimen as this regimen depends on the need and condition of the patient.

The invention provides a sufficiently potent formulation of aztreonam or a pharmaceutically acceptable salt thereof in a form of dry powder delivered as metered dose inhalation of aztreonam particles milled or spray dried to particle sizes predominantly within a range of 1 to 5µ. Such dry powder delivery is possible and preferable particularly for ambulatory inhalation as it simplifies the delivery process. Such delivery is convenient because it does not require any further handling such as diluting the dry powder or mixing the powder with a solvent, etc. Further, the dry powder inhalation utilizes the devices that are sufficiently small, fully portable and do not require, for example, an air compressor which is needed for a jet nebulizer. Additionally, the dry powder formulation has even longer shelf life than the liquid aztreonam formulation for aerosolization.

The dosing regimen for both aerosol and dry powder aztreonam comprises from one to four, typically, or more than four times daily, in untypical cases, administration of the aerosol or dry powder.

Severely impaired cystic fibrosis patients, for example, may be able to withstand only one inhalation at a time but could repeat this inhalation of small amount of aztreonam every two, three or four hours to obtain sufficient level of aztreonam in the lungs.

V. Devices for Delivery of Aerosolized Aztreonam

A primary requirement of this invention is to deliver aztreonam efficiently to the endobronchial space of airways in economic way. Thus, the invention requires that at least 30–50%, preferably 70–90% of the active drug, that is aztreonam or a salt thereof, subjected to nebulization is in fact delivered to a site where it asserts its therapeutic effect.

a) Nebulizers

The composition of the invention described above provides the drug formulated in a solution permitting delivery of a therapeutically efficient amount of the drug, provided that the aerosol generated by the nebulization meets criteria required for such efficient delivery. The apparatus (nebulizer) which aerosolizes the formulation of aztreonam thus becomes a very important part of the invention.

There are quite a few nebulizer types currently commercially available. Not all of them are suitable for practicing this invention.

A nebulizer is selected primarily on the basis of allowing the formation of aztreonam aerosol having a mass medium average diameter predominantly between 1 to 5µ. The delivered amount of aztreonam must be efficacious for treatment and prophylaxis of endobronchial infections, particularly those caused by susceptible bacteria. The selected nebulizer thus must be able to efficiently aerosolize the formulation which has salinity, osmotic strength, and pH adjusted as to permit generation of aztreonam aerosol that is therapeutically effective and well tolerated by patients. The negulizer must be able to handle the formulation having a smallest possible aerosolizable volume and still able to deliver effective dose of aztreonam to the site of the infection. Additionally, the aerosolized formulation must not impair the functionality of the airways and must minimize undesirable side effects.

The inability of certain nebulizers to nebulize therapeutic quantities of drugs into small and uniform particle size aerosols is well known. For efficacious delivery of aztreonam a range of aerosolized particles with MMAD needed to deliver the drug to the endobronchial space, the site of the infection, is between 1–5µ. Many commercially available nebulizers are able to aerosolize large volumes of the solution with an aim to deliver at least 10% of the volume to the endobronchial space by producing around 90% of large aerosol particles above 5µ with a very large number of particles being in the range of 50–100µ. These nebulizers are inefficient and not suitable for delivery of aztreonam according to this invention.

In order to be therapeutically effective, the majority of aerosolized aztreonam particles should not have larger mass medium average diameter (MMAD) than between 1 and 5µ. When the aerosol contains a large number of particles with a MMAD larger than 5µ, these are deposited in the upper airways decreasing the amount of antibiotic delivered to the site of infection in the lower respiratory tract.

Previously, two types of nebulizers, jet and ultrasonic, have been shown to be able to produce and deliver aerosol particles having sizes between 1 and 5µ. These particle size are optimal for treatment of pulmonary bacterial infection cause by gram-negative bacteria such as *Pseudomonas aeruginosa, Escherichia coli, Enterobacter* species, *Klebsiella pneumoniae, K. oxytoca, Proteus mirabilis, Pseudomonas aeruginosa, Serratia marcescens, Haemophilus influenzae, Burkholderia cepacia, Stenotrophomonas maltophilia, Alcaligenes xylosoxidans,* and multidrug resistant *Pseudomonas aeruginosa*. However, unless a specially formulated solution is used, these nebulizers typically need larger volumes to administer sufficient amount of drug to obtain a therapeutic effect. Therefore, without a specially formulated aztreonam the efficient delivery of aztreonam is not achieved.

Nebulizer suitable for practicing this invention must be able to nebulize a small volume of the formulation efficiently, that is into the aerosol particle size predominantly in the range from 1–5µ. Predominantly in this application means that at least 70% but preferably more than 90% of all generated aerosol particles are within 1–5µ range.

Jet and ultrasonic nebulizers can produce and deliver particles between the 1 and 5µ particle size. A jet nebulizer utilizes air pressure breakage of an aqueous aztreonam solution into aerosol droplets. An ultrasonic nebulizer utilizes shearing of the aqueous aztreonam solution by a piezoelectric crystal.

Typically, however, the jet nebulizers are only about 10% efficient under clinical conditions, while the ultrasonic nebulizer are only about 5% efficient. The amount deposited and absorbed in the lungs is thus a fraction of the 10% in spite of the large amounts of the drug placed in the nebulizer.

One type of nebulizer which is suitable and preferred for aztreonam delivery is an atomizing nebulizer which consists of a liquid storage container in fluid contact with the diaphragm and inhalation and exhalation valves. For administration of the aztreonam formulation, 1 to 5 ml of the formulation is placed in the storage container, aerosol generator is engaged which produces atomized aerosol of particle sizes selectively between 1 and 5µ.

Typical nebulizing devices suitable for practicing this invention include atomizing nebulizers, or modified jet nebulizers, ultrasonic nebulizers, electronic nebulizers, vibrating porous plate nebulizers, and energized dry powder inhalers modified for handling small volume of highly concentrated drug in a specific formulation having a specific pH, osmolality and salinity. Most preferred is the PARI inhalation nebulizer described in PCT/US00/29541 modified to meet the requirements of this invention.

b) Dry Powder Inhalers

Dry powder is administered as such using devices which deliver the dry powder directly to the lungs.

There are two major designs of dry powder inhalers. One design is the metering device in which a reservoir for the drug is placed within the device and the patient adds a dose of the drug into the inhalation chamber. The second is a factory-metered device in which each individual dose has been manufactured in a separate container. Both systems depend upon the formulation of drug into small particles of mass median diameters from 1 to 5 microns, and usually involve co-formulation with larger excipient particles (typically 100 micron diameter lactose particles). Drug powder is placed into the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs.

Current technology for dry powder inhalers is such that payload limits are around 100 mg of powder. The lack of long-term stability of aztreonam in an aqueous solution due to hydrolysis allows dry powder inhaler technology to become a preferred delivery vehicle for aztreonam dry powder.

C. Aerosol or Dry Powder Particle Size

Particle size of the aztreonam aerosol formulation is one of the most important aspect of the invention. If the particle size is larger than 5µ then the particles are deposited in upper airways. If the particle size of the aerosol is smaller the 1µ then it does not get deposited in the endobronchial space but continues to be delivered into the alveoli and may get transferred into the systemic blood circulation.

A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes. However, only some formulations of aztreonam can be efficiently nebulized as the devices are sensitive to pH and salinity.

In dry powder inhalers, the aztreonam dry powder prepared as described above in dosages from 1–100 mg, preferably from 10–50 mg of dry powder as particles having sizes between 1 and 5µ, is used directly.

D. Efficacy of Aztreonam Nebulization

Selection and choice of the nebulizer greatly effects efficacy of the inhalable aztreonam delivery.

A combination of an aerosol formulation of aztreonam and a nebulizing device significantly enhance the efficiency and speed of drug administration. Currently, for example the average time for administration of other aerosolized drugs, such as for example tobramycin, is 15–20 minutes per dose. The time required for this treatment represents a significant burden to the patient and contribute to reduced compliance with the BID regimen.

Furthermore, the nebulizer system used for tobramycin administration is less efficient than new atomizing devices. The total deposited dose of tobramycin in the lung is in the 12 to 15% range. Approximately 30% of the dispensed drug remains in the nebulizer at the end of treatment, and of the portion that is aerosolized, about 30% is emitted as particles too large or small to reach the lower airways.

The novel atomizing nebulizer, with an output of 8 to 10 microliters/seconds, or 0.48 to 0.60 ml/minute, is capable of delivering drug material 2 to 4 times faster than the prior nebulizers exemplarized by PARI LC plus nebulizer. Furthermore, the novel nebulizer is able to aerosolize approximately 90% of the dispensed dose, with 85% or more of the aerosol particles being within the size range required for lower airway deposition. As a result, administration of a specifically designed formulation of aztreonam using the atomizing nebulizer leads to substantial improvement in local delivery to the airways, to a shorter time required for delivery and, depending on the final concentration of aztreonam solution, reduces treatment time to as little as four minutes.

VI. Treatment of Pulmonary Bacterial Infections

This invention provides an efficacious treatment and prevention of acute and chronic pulmonary bacterial infections caused by *Pseudomonas aeruginosa, Escherichia coli, Klebsiella pneumoniae, Pseudomonas aeruginosa, Haemophilus influenzae, Proteus mirabilis, Enterobacter* species and *Serratia marcescens*, as well as infection caused by antibiotic resistant strains *Burkholderia cepacia, Stenotrophomonas maltophilia, Alcaligenes xylosoxidans*, and multidrug resistant *Pseudomonas aeruginosa*.

A. Two Modes of Inhalable Treatment

A method for treatment of pulmonary infections comprises administration of aztreonam in inhalable form whether by. aerosol or as a dry powder, several times a day. The aztreonam daily dose is between 1 and 500 mg/day, with exceptional dose up to 750 mg/day administered in from 1–50 mg/ml for aerosol and from 2 to 200 mg daily dose of dry powder administered in a dose of 1–100 mg/one treatment. The aztreonam dosage and dosing frequency depends on the type of bacterial infection, severity thereof, age of the patient, the conditions of the patient, etc. In case of cystic fibrosis patients where the lung air capacity is diminished, the dosing is more frequent with lower doses.

The dry powder formulation suitable for treatment of pulmonary infections comprises 1 to 200 mg, preferably about 10 to 100 mg, of powder in an amorphous or crystalline state in particle sizes between 1 and 5 microns in mass median average diameter necessary for efficacious delivery of aztreonam into the endobronchial space. The dry powder formulation is delivered one to four or more times daily, preferably twice daily. The dry powder formulation is temperature stable and has a physiologically acceptable pH of 4.5–7.5, preferably 5.5 to 7.0, and an over five year long shelf life.

B. Treatment of Infections in Patients with Suppurative Pulmonary Diseases

Aerosol therapy of this invention is particularly useful for treatment of patients suffering from suppurative pulmonary diseases and is especially suitable for treatment of patients with cystic fibrosis, bronchiectasis and those patients on the mechanical ventilation.

Previously, aerosol therapy for cystic fibrosis inhaled (ATCF) antibiotics have demonstrated significant benefit of such treatment to cystic fibrosis (CF) patients suffering from chronic pulmonary infections.

In the US, the most widely used and successful agent in this regard has been tobramycin, which has been shown to produce substantial improvements in lung function and other clinical parameters.

It has now been discovered that inhalable aztreonam provides successful treatment in cystic fibrosis, bronchiectasis or other suppurative pulmonary disease for pulmonary infections caused by gram-negative bacteria and particularly those caused by antibiotic resistant *Burkholderia cepacia, Stenotrophomonas maltophilia, Alcaligenes xylosoxidans* and multidrug resistant *Pseudomonas aeruginosa*.

Treatment of these multi-resistant bacterial infections with aerosolized aztreonam has been successful in eradication of the bacteria as described in Example 2.

Such treatment is stand alone or may be complementary treatment to other antibiotics, such as tobramycin, which upon extended use, results in the development of anti-tobramycin resistance. When the treatment with tobramycin is interspaced with periods of treatment with aztreonam, such resistance either does not develop or recedes.

C. Limitations of Current Aerosolized Antibiotics in Treatment of Cystic Fibrosis To date, an aminoglycoside tobramycin is the only antibiotic with FDA approval for administration as an aerosol. However, despite the benefits obtained in cystic fibrosis patients with administration of aerosolized tobramycin, its utility is somewhat limited.

First, frequent use of aminoglycosides to control pulmonary exacerbations leads to selective development of resistant Pseudomonas aeruginosa strains. The widespread emergence of such organisms is acknowledged as a growing crisis in the CF community. For example, 21% of patients screened from 69 different CF centers for the phase III tobramycin clinical trials had isolates resistant to tobramycin (MIC>16 µg/mL). Accordingly, many clinicians are reluctant to prescribe this aerosolized aminoglycoside as chronic suppressive therapy, fearing that it could further promote resistance and thus diminish the effectiveness of IV therapy. In order to reduce the risk of such treatment-emergent resistance, tobramycin therapy is restricted to cycles of 28 days on and 28 days off the drug.

A second limitation of aerosolized tobramycin is its lack of activity against several intrinsically tobramycin resistant bacteria, including *Stenotrophomonas maltophilia, Alcaligenes xylosoxidans,* and *Burkholderia cepacia*, the latter of which is widely recognized as a significant threat to cystic fibrosis patients. Cystic fibrosis patients infected with *Burkholderia cepacia* have an increased rate of mortality, and many experience a rapid fatal course, as described in *Am. J. Respir. Crit. Care Med.,* 160:1572–1577, (1999). Additionally, *Burkholderia cepacia* is a transmittable infection which can cause epidemic spread among cystic fibrosis patients. Therefore, a patient infected with *Burkholderia cepacia* must be isolated from other patients.

Aerosolized aztreonam does not induce resistance to aminoglycosides and has activity against resistant pathogens observed in cystic fibrosis patients.

An aerosolized aztreonam can either replace tobramycin, or be used as an alternative and intermittent treatment for tobramycin during the 28-day tobramycin free periods, which are required to prevent development of permanent resistance to tobramycin.

Aztreonam is an antibiotic with excellent activity against many aerobic gram-negative bacteria, including multi-resistant *Pseudomonas aeruginosa*. The spectrum of activity of aztreonam is similar to that of the aminoglycoside antibiotics tobramycin and gentamycin, and its antipseudomonal activity is comparable to ceftazidine.

Aztreonam resists destruction by most bacterial β-lactamases, which are the source of much treatment-emergent resistance to β-lactam antibiotics frequently appearing among hospitalized patients.

Aztreonam's activity against gram-negative bacteria, especially *Pseudomonas aeruginosa*, combined with its excellent safety profile makes it a good alternative to aminoglycosides in the treatment of chronic pulmonary infections among cystic fibrosis patients. Thus far, clinical use of aztreonam in CF patients has included IV administration of aztreonam as single agent therapy or in combination with other antibiotics for treatment of pulmonary exacerbations.

D. Advantages of Aztreonam as an Aerosolized Antibiotic

Aztreonam possesses several features that make it very attractive for aerosol administration to CF patients.

The first of these features stems from its mechanism of action, which, unlike aminoglycoside antibiotics, involves preferential binding to penicillin binding protein 3 (PBP3) and subsequent interference with bacterial cell wall synthesis. Because aztreonam's mechanism of action differs from that of tobramycin, its use does not contribute to emergence of aminoglycoside-resistant strains of *Pseudomonas aeruginosa*.

The second advantage of an aerosolized formulation of aztreonam is its activity against tobramycin resistant, and multidrug resistant *Pseudomonas aeruginosa*. When isolates from patients enrolled in the Phase II tobramycin trials were examined, nearly 75% of isolates with a tobramycin MIC>16 μg/mL were susceptible to aztreonam.

The third feature is aerosolized aztreonam ability to control intrinsically tobramycin resistant organisms, especially *Burkholderia cepacia*, which is considered resistant to the levels of aztreonam achieved by parenteral administration.

VII. In Vitro Testing

In order to test antibacterial activity of aerosolized aztreonam against multi-resistant strains of *Pseudomonas aeruginosa*, *Burkholderia cepacia*, *Stenotrophomonas maltophilia* and *Alcaligenes xylosoxidans*, the in vitro activities of aztreonam in concentrations corresponding to those achievable with inhalable aztreonam were tested against clinical isolates from cystic fibrosis patients.

The aztreonam aerosol delivery according to the invention achieves concentrations of aztreonam to reach levels from 500 to as high as 8000 μg/ml, with an average level around 2,000 μg/ml, of aztreonam in the sputum. These levels depend on the formulation as well as on the nebulizer used for aerosolization. With certain nebulizers the concentration of aztreonam can reach an average level of 5,000 μg/ml.

In vitro determined susceptibilities of the tested bacteria is predictive of clinical efficacy of inhaled aztreonam aerosol or dry powder.

Aztreonam kills by lysing cell walls as long as the local concentration of antibiotic exceeds the bacteria minimal inhibitory concentration (*Med. Clinics N. Am.*, 79:4, 733–743, (1995)).

The in vitro activity of high aztreonam concentrations against clinical isolates of *B. cepacia*, *S. maltophilia* and *A. xylosoxidans* was tested at the Children's Hospital and Regional Medical Center in Seattle, Wash. Testing was performed on broth microdilution trays made with 2 fold concentrations of aztreonam from 2 to 2048 μg/mL. *Staphylococcus aureus*, a gram positive organism, was used as a negative control. Detailed procedure used for testing is described in Example 1. Results are seen in Table 1.

TABLE 1

| Organism (# of isolates) | MIC Range | MIC50 | MIC90 |
| --- | --- | --- | --- |
| P. aeruginosa (54) | 2–1024 | 16 | 512 |
| B. cepacia (38) | 2–2048 | 32 | 512 |
| S. mallophilia (20) | 8–>2048 | 256 | >2048 |
| A. xylosoxidans (20) | 2 > 2048 | 256 | 2048 |
| S. aureus (20) | 512–2048 | 1024 | 2048 |

For testing, each microwell plate contained a 2-fold dilution, 2, 4, 8, 16, 32, 64, 128, 256, 512, 1024 and 2048 of aztreonam. Each plate containing the microwells was used to test one isolate of one organism.

Table shows the different species of bacteria tested for sensitivity, that is the ability of the antibiotic to inhibit its growth, to aztreonam, with the number of isolates for each species given in parenthesis. The column designated "MIC range" shows the range of the lower and upper limits of sensitivities seen in the tested isolates. The column designated MIC50 shows the median level of sensitivity for the most sensitive 50% isolates. The final column, designated MIC90, shows the median value for the level of sensitivity for the most sensitive 90% of the isolates.

Table 1 shows results of comparative in vitro activity of aztreonam against clinical isolates obtained from cystic fibrosis patients.

For interpretation of this data, these values which represent what concentration of aztreonam is required to inhibit growth of bacteria are compared with the concentrations of aztreonam obtainable by the different routes of administration. Thus, for intravenous administration of aztreonam, the serum level following administration of 2 g of aztreonam, the maximum allowed intravenous dose, the serum level is peak is 256 μg/ml and then declines rapidly. At six hours following the administration, the aztreonam level in the serum is in the range of 16 μg/ml. For safety reasons, intravenous aztreonam can only be administered every six hours. With the possible exception of *Pseudomonas aeruginosa* that has a MIC50 of 16 μg/ml, all other organisms would be predominantly resistant to intravenous aztreonam, as their level of resistance exceeds even the peak concentration (256 μg/ml) of serum concentration of sputum of aztreonam following intravenous administration. Since, however, the bacteria resistance is relative to drug concentration, for aerosol administration, the peak concentration should be at least in the 500 to 2000 μg/ml range. Such range is achieved with the doses of aztreonam and the formulation of the invention combined with the efficient nebulizer, according to this invention. At the 500–2000 μg/ml concentration in the sputum, the aerosol therapy according to this invention is able to treat most endobronchial infections caused by gram-negative bacteria, specifically those bacteria listed in Table 1, with exception, of course, of *Staphylococus aurelius*.

The MIC50 and MIC90 have shown that treatment of *P. aeruginosa* with inhalable aztreonam eradicates most *P. aeruginosa* isolates with the high concentrations of aztreonam in sputum of cystic fibrosis patients obtainable after aerosol delivery. The data obtained for *Burkholderia cepacia* isolate indicated that at least half of patients would be expected to respond to such treatment with eradication of the bacteria. If sufficiently high concentrations of aztreonam are delivered to the lung, the percentage is expected to be higher. Since the *Burkholderia cepacia* infection is now viewed as a largely untreatable condition, treatment with inhalable aztreonam by aerosol is the first documented efficacious therapy.

The results obtained in these studies are surprising and unexpected as there is no indication in the literature that *Burkholderia cepacia* is susceptible to treatment with aztreonam. The data also shows that some isolates of *S. maltophilia* and *A. xyloxidans* respond to high concentration of aztreonam.

Inhalation of aztreonam according to the invention permits reaching concentrations of aztreonam in the sputum as high as 2000–5,000 μ/mL. The sputum aztreonam levels achieved via aerosol administration exceed those required to inhibit organisms responsible for otherwise untreatable infections in CF patients.

Furthermore, aztreonam delivered by inhalation to all patients with *Burkholderia cepacia* and/or *S. maltophilia* and/or *A. xyloxidans* together with other antibiotics whether administered systemically parenterally or by inhalation contributes to synergy of such treatment. A combination of inhalable aztreonam with other antibiotics provides another therapeutic approach to treat multi-resistant bacterial strains.

The studies described herein demonstrated that the concentrations of aztreonam achieved following aerosol administration have activity against *Burkholderia cepacia* isolated from CF patients' sputum as well as against other bacteria which are largely resistant to treatment with other antibiotics.

The MIC50 and MIC90 observed for a gram positive bacteria, *Staphylococcus aureus*, show that high concentrations of aztreonam had some activity against this gram positive bacteria. These findings, however, have no great significance as there are many other drugs with reasonable efficacy against *Staphyloccocus aureus*.

VII. In vivo Testing

The infections requiring particular attention are infections caused by and include *B. cepacia, S. maltophilia* and *A. xylosoxidans*, as well as multi-resistant strains of Pseudomonas aeruginosa, the most clinical significant infection is the former.

In order to determine if an appropriately formulated aztreonam for aerosolization could become effective for treatment of these rare but very resistant bacterial strains, the treatment with aerosolized aztreonam was initiated and tested in a cystic fibrosis patient having a severe Burkholderia cepacia infection which did not respond to any treatment. The clinical treatment and results obtained with an aerosolized aztreonam is described in Example 2.

Utility

The method of treatment and the inhalable aztreonam compositions disclosed herein is suitable for treatment of respiratory tract infections caused by *Burkholderia cepacia, Stenotrophomonas maltophilia, Alcaligenes xylosoxidans*, and multidrug resistant *Pseudomonas aeruginosa* as well as for treatment of other pulmonary infections caused by gram-negative bacteria.

EXAMPLE 1

In vitro Testing of Isolates from Cystic Fibrosis Patients

This example describes procedure used for in vitro studies of bacterial isolates obtained from cystic fibrosis patients.

Bacterial respiratory tract isolates (144) from patients with CF that had been stored at −70° C. were cultivated by two consecutive overnight passages at 37° C. on 5% blood agar (Remel, Lenexa, Kans.).

Minimal inhibitory concentrations (MIC's) were determined by the following steps:

MIC Antimicrobial Testing Aerobic Organisms

1. MIC trays were brought to room temperature.

2. 3.0 ml physiological saline was inoculated with an 18–24 h culture of organism to be tested to a turbidity equal to a 0.5 McFarland Standard ($1.5 \times 10^8$ CFU/ml). This corresponds to an OD600 of 80–88% transmission.

3. Within 15 minutes of preparation, the adjusted inoculum suspension was diluted by transferring 100 ml into a 2.9 ml diluent of sterile water.

4. The suspension was gently mixed by inversion and 10 ml was dispensed into each MIC well having initial volume of 100 µl. The final concentration in each well was equal to $5 \times 10^5$ CFU/ml or $5 \times 10^4$ CFU/well.

5. Trays were incubated aerobically at 37° C. for 16–20 hours. The same incubation temperature was maintained for all cultures. Microdilution trays were not stacked more than four high.

6. Antimicrobial endpoint was read and recorded as the first well showing no readily visible growth or haze as detected by the unaided eye.

7. The microdilution trays were contacted with 2 fold concentrations of aztreonam from 2 to 2048 mg/mL. Each microwell plate was treated with a 2-fold dilution of aztreonam in following amounts: 2, 4, 8, 16, 32, 64, 128, 256, 512, 1024 and 2048 µg/ml. Each plate containing the microwells was used to test one isolate of one organism.

8. Results were read and recorded.

EXAMPLE 2

Clinical Treatment of Patient with *Burkholderia cepacia*

This example describes a first finding of efficacy of the aerosolized aztreonam treatment of a cystic fibrosis patient suffering from resistant Burkholderia cepacia.

The patient was a 20-year-old female with cystic fibrosis and end stage lung disease. She had been diagnosed with *Burkholderia cepacia* pulmonary infections that had become resistant to all known intravenous, oral and inhaled antibiotics. She had two-documented genetically different strains of *Burkholderia cepacia*. For this reason the patient was rejected as a candidate for a lung transplant.

The patient was provided with a formulation of the invention comprising 200 mg/ml of aztreonam and instructed to use this formulation in 3 to 5 ml of diluent and use it in an air compressor powered breath enhanced jet nebulizer and take the therapy twice a day. This type of nebulizer only delivers about 10 to 20% of the dose placed in the nebulizers to the lungs, however, that was only nebulizer available to the patient for home treatment.

After three months of continuous twice a day therapy, the pulmonary infection was successfully treated and no evidence of *Burkholderia cepacia* could be detected. The patient was considered treated from the infection and eventually underwent a successful lung transplant procedure.

There was no postoperative reoccurrence or relapse of the *Burkholderia cepacia* infection despite of intensive immunosuppression therapy following the transplantation.

These findings were surprising since previous use of commercially available aztreonam in an older generation delivered in even less efficient nebulizers did not lead to eradication of *P. aeruginosa* as described in *Clinics Chest Med.*, 19:473–86, (September 1998). In this trial, the authors stopped therapy at the development of any aztreonam resistance rather than continuing treating these patients. Prior work did not test or speculate that this therapy could be effective in treating other gram negative bacteria including *Burkholderia cepacia, S. maltophilia, X. xylosoxidans*, or other multidrug resistant pseudomonas infections.

The results obtained with treatment of the above patient are even more surprising in that the eradication of *Burkholderia cepacia* is extremely rare occurrence, particularly when the infection is well established as was in the case of this patient.

EXAMPLE 3

Preparation of Aztreonam Dry Powder

This example provide methods and procedures used for preparation of aztreonam containing inhalable dry powder.

For dry powder formulation of the invention, a purified aztreonam antibiotic, or a pharmaceutically acceptable salt thereof, is milled to a powder having mass median average diameters ranging from 1 to 5μ by media milling, jet milling spray drying, or particle precipitation techniques.

Particle size determinations is made using a multi-stage Anderson cascade impactor.

Media milling may be accomplished by placing the drug substance into a mill containing, for example, stainless steel or ceramic balls and rotating or tumbling the material until the desired drug particle size ranges are achieved.

Jet milling uses very high pressure air streams to collide particles with one another, with fine particles of the desired size being recovered from the mill.

Spray drying is achieved by spraying a fine mist of drug solution onto a support and drying the particles. The particles are then collected.

Particle precipitation is achieved by adding a co-solvent to spray dried particles. The solubility of the drug falls to the point where solid drug particles are formed. The particles are collected by filtration or centrifugation. Precipitation has the advantage of being highly reproducible and can be performed under low temperature conditions, which reduce degradation.

EXAMPLE 4

Dry Powder Inhalators

The dry powder formulations of the invention may be used directly in metered dose or dry powder inhalers.

A metered dose inhaler consists of three components: a canister containing the propellant drug suspension, a metering valve designed to deliver accurately metered volumes of the propellant suspension, and an oral adapter which contains a spray orifice from which the metered dose is delivered. In the rest position, the metering chamber of the valve is connected to the drug suspension reservoir via a filling groove or orifice. On depression of the valve this filling groove is sealed and the metering chamber is exposed to atmospheric pressure via the spray orifice in the oral adapter and the valve stem orifice. This rapid pressure reduction leads to flash boiling of the propellant and expulsion of the rapidly expanding mixture from the metering chamber. The liquid/vapor mixture then enters the expansion chamber which is constituted by the internal volume of the valve stem and the oral adapter. The mixture undergoes further expansion before being expelled, under its own pressure, from the spray nozzle. On exit from the spray orifice, the liquid ligaments which are embedded in propellant vapor are torn apart by aerodynamic forces. Typically, at this stage, the droplets are 20 to 30μ in diameter and are moving at the velocity of sound of the two-phase vapor liquid mixture (approximately 30 meters per second). As the cloud of droplets moves away from the spray nozzle, it entrains air from the surroundings and decelerates, while the propellant evaporates through evaporation, the entrained droplets eventually reach their residual diameter.

At this point, the particles/droplets consist of a powdered drug core coated with surfactant. Depending on the concentration and the size of the suspended material the powdered drug core consists of either individual drug particles or aggregates. Currently, meter dose inhaler technology is optimized to deliver masses of 80 to 100 micrograms of drug, with an upper limitation of 1 mg of drug deliverable.

An alternated route of dry powder delivery is by dry powder inhalers. There are two major designs of dry power inhalers, device-metering designs in which a reservoir of drug is stored within the device and the patient "loads" a dose of the device into the inhalation chamber, and factory-metered devices in which each individual dose has been manufactured in a separate container. Both systems depend upon the formulation of drug into small particles of mass median diameters from 1 to 5 microns, and usually involve co-formulation with large excipient particles (typically 100 micron diameter lactose particles). Drug powder is supplied into the inhalation chamber (either by device metering or by breakage of a factory-metering dosage) and the inspiratory flow of the patient accelerates the powder out of the device and into the oral cavity. Non-laminar flow characteristics of the powder path cause the excipient-drug aggregate to decompose, and the mass of the large excipient particles causes their impaction at the back of the throat, while the inhaler drug particles are deposited deep in the lungs. Current technology for dry powder inhalers is such that payload limits are around 50 mg of powder (of which drug is usually a partial component by mass). Excipients commonly used are lactose, however in the case of aztreonam free base the addition of the amino acids lysine or leucine will lead to better powder formation.

Effective dosage levels of aztreonam antibiotic for dry powder inhalation and metered dose inhalation result in the delivery of at least about 25 mg, and more preferable about 50 to about 100 mg of aztreonam antibiotic compound to the lung of the patient receiving treatment. Depending on the efficiency of the dry powder delivery device, dry powder formulations suitable for use in the invention comprise from about 1.0 to about 250 mg, preferably from about 10 to about 100 mg of powder in an amorphous or crystalline state in particle sizes between 1 and 5 microns in mass median average diameter necessary for efficacious delivery of the antibiotic into the endobronchial space. The dry powder formulation may be delivered from 1 to 4 times daily, preferably twice daily, for a period of at least one day, more preferably at least 5 days and most preferably at least fourteen days or longer. The dry powder formulations are temperature stable and have a physiologically acceptable pH of 4.0 to 7.5, preferably 5.5 to 7.0, and long shelf lives.

EXAMPLE 5

Preparation of Aztreonam Sodium Salt

This example describes procedure used for preparation of aztreonam sodium salt.

To a solution of 10 g (23 mmol) of aztreonam in 100 mL of MeOH cooled in an ice bath was added dropwise 23 mL (23 mmol, 1.0 eq) of 1N sodium hydroxide solution. The resulting solution was warmed to ambient temperature over a period of 30 min, and then the solvent was removed under reduced pressure. Diethylether (50 mL) was added and the slurry concentrated. This step was repeated four times to provide a yield of 10.1 g (96%) of aztreonam sodium salt as a white powder.

EXAMPLE 6

Preparation of Aztreonam Sodium Salt Solutions

This example describes procedure used for preparation of aztreonam sodium salt solution.

Aztreonam (10 g, 23 mM) free base was added to a tared 100 mL Erlenmeyer flask. Methanol (25 mL) was added to the flask with agitation by magnetic stirrer. 1N sodium hydroxide (23 mL, 1 equivalent) was gradually added while stirring. When solution was clear, it was removed from stir plate and the excess solvents were removed under reduced pressure to give a dry solid. Deionized water (166 mL) was added dropwise to the dry solid and the pH of the resulting solution was adjusted to the desired value of 6.5 by dropwise addition of 1N sulfuric acid while monitoring with a pH meter. The above procedure was used to prepare aztreonam salt solutions at 60 mg/mL by adjusting the weight of aztreonam and the volume of 1N sodium hydroxide.

EXAMPLE 7

Aztreonam Formulation

This example illustrates preparation of the aztreonam containing formulation of the invention.

1. Hot water for injection (WFI) was thoroughly flushed through 20 L Millipore product vessel.
2. Aztreonam potency (g/L) was assayed, and its efficacy determined.
3. Aztreonam was added to a wide mouth specimen bottle and label of product vessel in the accurately weighed amount.
4. 11.25 kg of WFI was dispersed into a clean 20L Millipore product vessel.
5. With moderate agitation, 33.75 g sodium chloride, USP, was slowly added and mixed until dissolved.
6. WFI was added to the product vessel to 12 kg and mixed for 5 minutes.
7. With continual mixing, 100 mL 5N of sulfuric acid ($H_2SO_4$) was carefully added for each liter of WFI in the final formulation.
8. Product vessel was sparged with nitrogen ($N_2$).
9. After approximately 15 minutes of sparging, dissolved oxygen ($O_2$) was measured by continuous monitoring of dissolved oxygen in the tank, using a probe.
10. Measuring of dissolved $O_2$ was continued until five (5) consecutive measurements <3 ppm dissolved $O_2$.
11. With continuous sparging of $N_2$ and moderate mixing, the 562.5 g (50 g/L) aztreonam was added and mixed until dissolved.
12. 20 mL sample from product formulation was removed and pH was measured. Product formulation was adjusted to final pH value of 6.0.
13. An aliquot of product formula was sampled and analyzed for aztreonam concentration.
14. An aliquot of product formula was analyzed for pH.
15. An aliquot of product formula was analyzed for dissolved $O_2$ (in triplicate).
16. When the batch met quality control testing criteria, the product was released for use.
17. The product was frozen to −20° C. and kept at this temperature or below until the actual use.

EXAMPLE 8

Testing Nebulizers

A clinical study is conducted in order to determine the concentration of aztreonam in the aerosol formulation required to achieve a sputum concentration between 500μg/gm and 2000 μg/gm sputum at 10 min post-completion of aerosol administration using an atomizing, ultrasonic or jet nebulizer.

In this study, cystic fibrosis patients receive serial doses of 250 mg aztreonam (5 ml of a 50 mg/ml solution in ¼ NS) from each of the nebulizers. The doses are separated by at least 2 days and not more than 5 days. Peak serum and sputum concentrations are assessed.

EXAMPLE 9

Clinical Trial Protocol

This example describes a protocol used for clinical trial and to compare the pharmacokinetics of increasing dosage of an aztreonam formulation administered by the PARI electronic nebulizer to patients with cystic fibrosis.

The primary aim of this study is to determine which of the tested dose levels delivered by aerosol can deliver sufficient amount of aztreonam or a salt thereof to achieve a mean peak sputum aztreonam concentration of 2000 μg/gm or greater measured 10 minutes after the completion of nebulization in patients with CF.

The secondary aim is to determine whether the aztreonam concentration required to achieve a mean peak sputum concentration of 2000 μg/gm or greater is safe and well tolerated by the patient.

Study Design

This is an open label, multicenter, randomized, dose escalation study.

Each arm is different dose. Two arms deliver the same aztreonam formulation.

1. 0.5 ml of aztreonam solution of 50 mg/ml
2. 1.0 ml of aztreonam solution of 50 mg/ml
3. 2.0 ml of aztreonam solution of 50 mg/ml
4. 3.0 ml of aztreonam solution of 50 mg/ml
5. 4.0 ml of aztreonam solution of 50 mg/ml
6. 5.0 ml of aztreonam solution of 50 mg/ml Efficacy and Safety Assessment In this study, the following efficacy and safety parameters are assessed:

The efficacy is determined for each nebulizer by measuring concentration of aztreonam in sputum 10 minutes after completion of nebulization. Mean concentration of 2000 μg/gm of sputum is considered adequate.

The safety parameters assessed:

1. Incidence of treatment related adverse reactions occurring during the administration of the aerosolized aztreonam at the different dose levels.
2. Acute bronchospasm at the time of drug administration.
3. Absorption of aztreonam into the systemic circulation.

Each patient receives in random order at least one administration. Each aerosol administration is separated by a minimum of 48 hr. Sputum samples are collected at baseline, 1, 2, 4 and 6 hours post-completion of the aerosol drug administration to measure aztreonam concentration. Serum samples are collected at baseline, 1, 2, 4 and 6 hours post-completion of aerosol administration to measure aztreonam levels.

Airway irritation and acute bronchospasm are assessed by measuring spirometry immediately prior to and 30 min post-completion of aerosol administration. A decrease in forced expired volume in one second (FEV1) >15% in the 30 min spirometry test is considered evidence of bronchospasm.

The primary objective of this study is to determine if and at what dose the PARI electronic nebulizer tested can aerosolize sufficient aztreonam sulfate to achieve a mean peak sputum aztreonam concentration of 2000 μg/gm or greater in at least 85% of patients with CF measured 10 minutes after the completion of nebulization.

The second objective is to determine whether the aztreonam concentration required to achieve a mean peak sputum concentration of 2000 μg/gm or greater is safe and well tolerated by the patient. Safety is defined as a lack of acute bronchospasm and minimal systemic absorption.

Patient Treatment

All patients with underlying disease of cystic fibrosis (CF), confirmed at entry by the inclusion/exclusion criteria specified in this protocol, are eligible for enrollment into the study. Investigators at the participating CF centers select patients that meet all of the inclusion criteria and one of the exclusion criteria.

Eligible patients are admitted to the study center on the day of the study and receive aerosol therapy if they fulfilled entrance criteria.

Physical exam is administered by a physician or RC nurse prior to initial aerosol treatment only.

Vital signs, height, weight, oximetry, assessment of current respiratory status and brief medical history are used.

Sputum and serum samples are collected to measure baseline aztreonam concentrations.

Patients are sitting upright and use nose clips during the aerosol administration.

The total duration of time and the number of inhalations required to complete the aerosol treatment are recorded.

Any evidence of wheezing or respiratory distress are recorded as well as number of rest periods required by the subject because of dyspnea or excessive coughing during the administration period.

Immediately after completing the aerosol therapy, the subject rinse with 30 ml of normal saline through the mount, gargled for 5–10 seconds and expectorated the rinse. This is repeated for a total of three rinses.

Sputum specimens are collected at 10 minutes after rinsing oral cavity and 2 hours after completion of the aerosol drug administration.

Serum is collected at 1 and 2 hours after completion of the aerosol drug administration for determination of the aztreonam levels.

Spirometry is obtained 30 minutes following completion of the aerosol drug administration.

Following the last aerosol treatment of the study, patients receive a brief physical exam after post-spirometry has been measured.

What is claimed is:

1. An inhalable aerosol comprising from about 1 to about 250 mg of purified aztreonam or a pharmaceutically acceptable salt thereof in a dry powder form dissolved in a saline solution per one dose, said aerosol suitable for treatment of pulmonary bacterial infections caused by gram-negative bacteria *Burkholderia cepacia, Stenotrophomonas maltophilia, Alcaligenes xylosoxidans*, and multidrug resistant *Pseudomonas aeruginosa*, wherein said pharmaceutically acceptable salt is selected from the group consisting of acetate, adipate, alginate, citrate, aspartate, benzoate, benzenesulfonate, bisulfate, bytyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lysinate, maleate, methanesulfonate, nicotinate, 2-napthalenesulfonate, oxalate, pamoate, pectinate, persulfate, 3-phenylpropionate, picrate, pivalate, propionate, succinate, tartrate, thiocyanate, p-toluenesulfonate and undecanoate.

2. The aerosol of claim 1 comprising from about 1 to about 200 mg or aztreonam or the pharmaceutically acceptable salt thereof per one dose is administered once, two, three or four times a day, with a proviso that when said aerosol is administered more than three times a day, the total dose of aztreonam or the salt thereof does not exceeds 750 mg a day.

3. The aerosol of claim 2 wherein the pharmaceutically acceptable salt is lysinate.

4. The aerosol of claim 3 wherein aztreonam or the salt thereof is dissolved in from about 1 to about 5 ml of an aerosolable solution comprising at least 0.09% of sodium chloride, or an equivalent amount of bromine, iodine or bicarbonate salt.

5. The aerosol of claim 4 wherein said aerosolable solution is a normal saline comprising 0.9% of sodium chloride or diluted saline comprising from about 0.1 to about 0.45% sodium chloride.

6. The aerosol of claim 5 wherein the aerosolable solution has a pH from about 4.5 to about 7.5.

7. The aerosol of claim 6 wherein the aerosolable solution has a pH from about 5.5 to about 7.

8. The aerosol of claim 7 nebulized into an aerosol having a particle size with a mass medium average diameter from about 1 to about 5 μ.

9. The aerosol of claim 8 wherein aztreonam or the salt thereof are provided in the dry powder form suitable for dissolving in the diluted saline to form an isotonic solution, each the powder and the saline supplied separately and mixed before aerosolization.

10. The aerosol of claim 4 wherein the aerosolable solution is an aqueous solution of the bicarbonate salt.

11. A method for treatment of pulmonary infections caused by gram-negative bacteria *Burkholderia cepacia, Stenotrophomonas maltophilia, Alcaligenes xylosoxidans*, and multidrug resistant *Pseudornonas aeruginosa*, said method comprising steps:

a. preparing an aztreonam aerosol comprising from about 1 to about 250 mg of purified aztreonam or a pharmaceutically acceptable salt thereof in a dry powder form, wherein said pharmaceutically acceptable salt is selected from the group consisting of acetate, adipate, alginate, citrate, aspartate, benzoate, benzenesulfonate, bisulfate, bytyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesul fonate, lysinate, maleate, methanesulfonate, nicotinate, 2-napthalenesulfonate, oxalate, pamoate, pectinate, persulfate, 3-phenylpropionate, picrate, pivalate, propionate, succinate, tartrate, thiocyanate, p-toluenesulfonate and undecanoate, said aztreonam or salt dry powder dissolved in from about 1 to about 5 ml of solution containing from about 0.1 to about 0.9% of chloride or an equivalent thereof; and b. delivering said aztreonam or aztreonam salt aerosol to the lung endobronchial space of airways of a patient in need thereof by nebulization of said aerosol into aerosol particles having a mass medium average diameter between about 1 and about 5μ.

12. The method of claim 11 wherein said aerosol is administered one to twelve times a day, provided that a total daily dose of aztreonam is not higher than 750 mg.

13. The method of claim 12 wherein aztreonam pharmaceutically acceptable salt is lysinate.

14. The method of claim 13 wherein the aztreonam aerosol comprises from about 2 to about 500 mg of aztreonam or a pharmaceutically acceptable salt thereof, dissolved in from about 1 to about 5 ml of solution containing from about 0.09 to about 0.9%, w/v, of sodium chloride or an equivalent amount of bromine, iodine or bicarbonate salt.

15. The method of claim 14 wherein said aerosol has pH between about 4.5 and 7.5 and saline solution contains from about 0.1 to about 0.45% of chloride.

16. The method of claim 13 wherein said aerosol has pH between about 5.5 and 7.

17. The method of claim 16 wherein said aerosol is delivered by a jet, electronic, ultrasonic or atomization nebulizer.

18. The method of claim 17 comprising administration of from about 10 to about 100 mg of aztreonam in the aerosol one to four times a day delivered by the electronic nebulizer.

19. The method of claim 18 comprising administration of from about 10 to about 100 mg of aztreonam in the aerosol one to four times a day.

20. The method of claim 11 wherein a delivered dose of aztreonam or the pharmaceutically acceptable salt thereof into the lung endobronchial space of airways during one administration is at least 25 mg of aztreonam or the salt thereof.

21. The method of claim 11 suitable for treatment of infections caused by the gram-negative bacteria in patients with cystic fibrosis, bronchiectasis, or in the patients on ventilators with pneumonia.

22. A method of treatment for pulmonary infections caused by gram-negative bacteria *Burkholderia cepacia*, *Stenotrophomonas maltophilia*, *Alcaligenes xylosoxidans*, and multidrug resistant *Pseudomonas aeruginosa*, said method comprising steps:

a. preparing an inhalable aztreonam aerosol consisting of from about 1 to about 200 mg of purified aztreonam base, or a pharmaceutically acceptable salt thereof selected from the group consisting of acetate, adipate, alginate, aspartate, benzoate, benzenesulfonate, bisulfate, butyrate, camphorate, camphorsulfonate, chloride, citrate, cyclopentanepropionate, digluconate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, lysinate, maleate, methanesulfonate, nicotinate, 2-napthalenesulfonate, oxalate, pamoate, pectinate, persulfate, 3-phenylpropionate, picrate, pivalate, phosphate, propionate, succinate, sulphate, tartrate, thiocyanate, p-toluenesulfonate and undecanoate, said aztreonam or the salt thereof dissolved in from about 1 to about 5 ml of an aqueous solution having pH from 5.5 to 7.0; and b. delivering said inhalable aztreonam aerosol to the lung endobronchial space of airways of a patient in need thereof by a jet, electronic, ultrasonic or atomization nebulizer in an aerosol having particle sizes between 1 and 5 microns.

23. The method of claim 22 wherein said aztreonam salt is lysinate and the aqueous solution is a normal or diluted saline comprising from 0.225% to 0.9% of sodium chloride.

24. The method of claim 23 wherein the inhalable aztreonam aerosol is delivered one to twelve times a day, provided that if said aerosol is delivered more then twice a day, a total dose of aztreonam is not higher than 500 mg a day.

25. The method of claim 24 wherein said aztreonam aerosol comprises from about 1 to about 100 mg of the aztreonam per one dosage.

26. The method of claim 25 said aztreonam aerosol comprises from about 10 to about 50 mg of the aztreonam per one dosage.

27. The method of claim 26 wherein said aztreonam aerosol is delivered once, twice, three or four times a day.

28. The method of claim 27 wherein said aerosol is delivered by the jet nebulizer.

29. The method of claim 27 wherein said aerosol is delivered by the electronic nebulizer.

30. The method of claim 22 wherein a delivered dose of aztreonam or the pharmaceutically acceptable salt thereof into the lung endobronchial space of airways during one administration is at least 25 mg of aztreonam or the salt thereof.

* * * * *

UNITED STATES PATENT AND TRADEMARK OFFICE
CERTIFICATE OF CORRECTION

PATENT NO. : 7,208,141 B2  Page 1 of 1
APPLICATION NO. : 10/654815
DATED : April 24, 2007
INVENTOR(S) : Alan Bruce Montgomery It is certified that error appears in the above-identified patent and that said Letters Patent is hereby corrected as shown below:

At column 7, line 10, in formula (I),

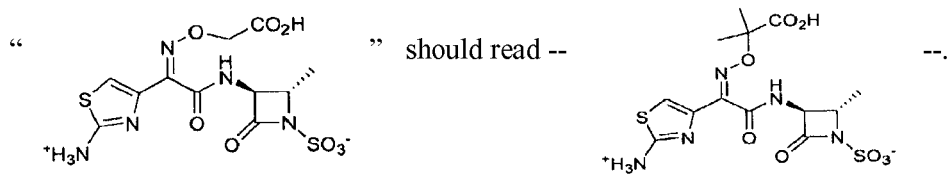

At column 32, the third line of Claim 8, "5µ" should read --5µm--.

At column 33, line 9, "5µ" should read --5µm--.

At column 34, the third line of Claim 24, "then" should read --than--.

Signed and Sealed this

Twenty-seventh Day of May, 2008

JON W. DUDAS
*Director of the United States Patent and Trademark Office*